United States Patent
Nanaumi et al.

[11] Patent Number: 5,965,802
[45] Date of Patent: Oct. 12, 1999

[54] NO_x SENSOR FOR EXHAUST GAS, AND PROCESS FOR PRODUCING THE SAME

[75] Inventors: Masaaki Nanaumi; Hiroshi Takeshita; Norihiro Ohta; Noriko Ohta, heiress of Norihiro Ohta; Yoshikazu Fujisawa; Yoichi Asano; Yoshiaki Takagi, all of Saitama, Japan

[73] Assignee: Honda Giken Kogyo Kabushiki Kaisha, Tokyo, Japan

[21] Appl. No.: 08/966,099

[22] Filed: Nov. 7, 1997

[30] Foreign Application Priority Data

Nov. 7, 1996 [JP] Japan ................................. 8-311357

[51] Int. Cl.$^6$ .......................... G01N 27/12; G01N 29/00; H01C 7/00
[52] U.S. Cl. ...................... 73/23.2; 73/31.06; 73/31.02; 422/90; 422/98; 29/25.01; 324/71.5; 338/34
[58] Field of Search .................. 73/23.2, 31.05, 73/31.06, 23.31, 31.02, 23.32; 422/88, 90, 94, 98; 427/126.1, 126.3, 376.2; 436/137; 338/34; 324/71.5, 691, 609; 29/25.01

[56] References Cited

U.S. PATENT DOCUMENTS

| | | | |
|---|---|---|---|
| 4,251,225 | 2/1981 | Handa et al. | 23/232 E |
| 4,381,922 | 5/1983 | Frey et al. | 422/98 |
| 4,543,273 | 9/1985 | Handa et al. | 427/126.3 |
| 4,794,323 | 12/1988 | Zhou et al. | 324/71.5 |
| 4,944,273 | 7/1990 | Baresel et al. | 123/440 |
| 4,977,658 | 12/1990 | Awano et al. | 29/25.01 |
| 5,222,388 | 6/1993 | Sinha et al. | 73/23.2 |
| 5,342,701 | 8/1994 | Miremadi et al. | 428/701 |
| 5,486,336 | 1/1996 | Dalla Betta et al. | 422/90 |
| 5,580,433 | 12/1996 | Baker et al. | 204/425 |
| 5,624,640 | 4/1997 | Potthast et al. | 422/90 |
| 5,635,628 | 6/1997 | Fleischer et al. | 73/31.06 |
| 5,698,771 | 12/1997 | Shields et al. | 73/31.05 |
| 5,726,347 | 3/1998 | DeHaan | 73/31.06 |
| 5,734,091 | 3/1998 | Hudo et al. | 73/23.2 |
| 5,783,154 | 7/1998 | Althainz et al. | 422/98 |
| 5,810,984 | 9/1998 | Hudo et al. | 204/426 |
| 5,811,662 | 9/1998 | Williams et al. | 73/31.06 |
| 5,814,281 | 9/1998 | Williams et al. | 422/88 |

FOREIGN PATENT DOCUMENTS 8-15199  1/1996  Japan .

Primary Examiner—Hezron Williams
Assistant Examiner—J. David Wiggins
Attorney, Agent, or Firm—Lyon & Lyon LLP

[57] ABSTRACT

An NO_x sensor is produced by sintering a plurality of columnar crystals of β-type $Nb_2O_5$. The average value M of aspect ratios b/a (wherein a represents a width and b represents a length) in the columnar crystals is set in a range of $2.11 < M \leq 5$. The NO_x sensor has a high sensitivity to NO_x via an enhancement attained by control of crystal type and structure.

15 Claims, 18 Drawing Sheets

COMPARATIVE EXAMPLE 4

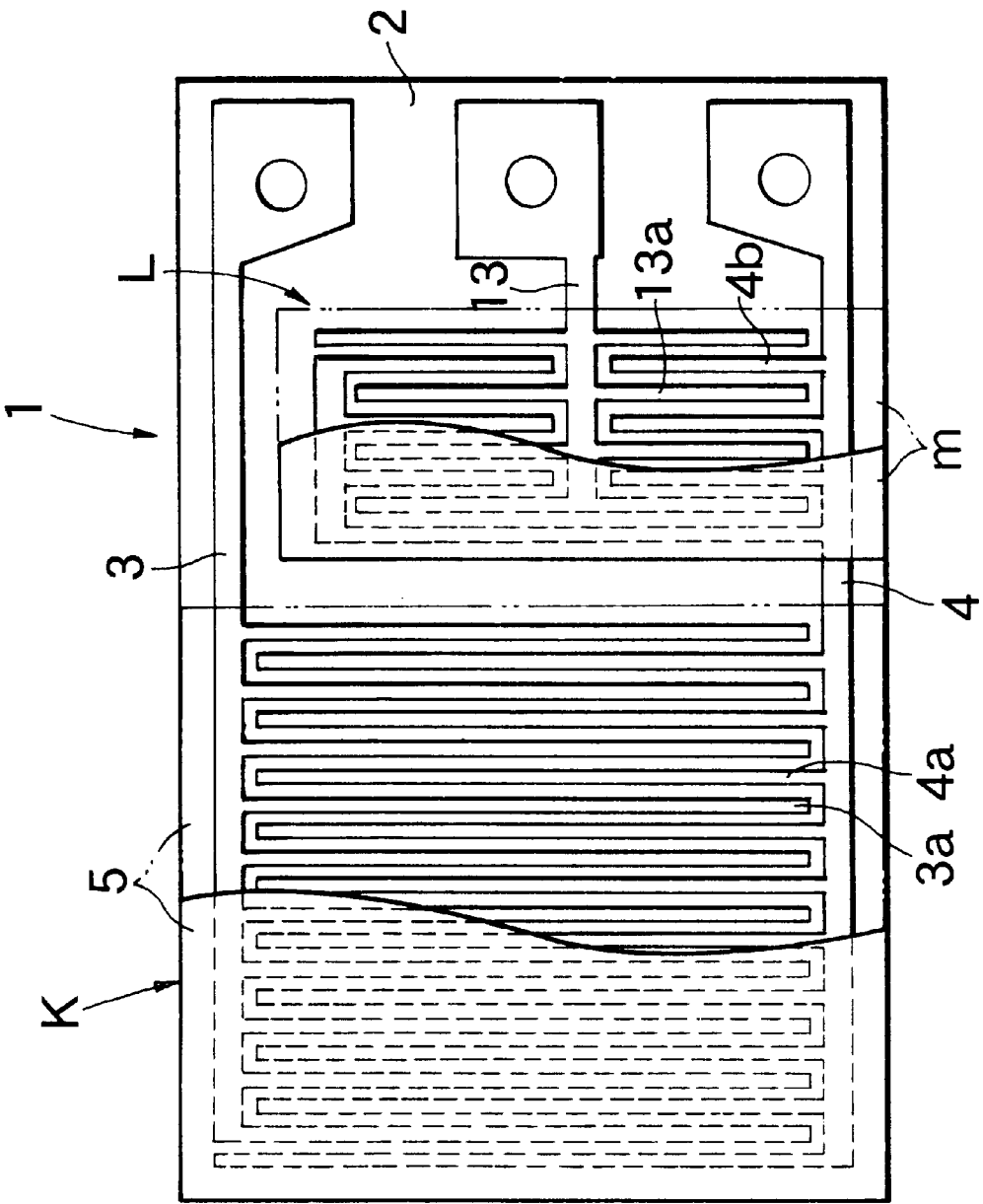

$NO_x$ SENSOR FOR EXHAUST GAS, AND PROCESS FOR PRODUCING THE SAME

BACKGROUND OF THE INVENTION

1. Field of the Invention

The present invention relates to an $NO_x$ (nitrogen oxides) sensor for an exhaust gas in an automobile vehicle, and a process for producing the same.

2. Description of the Related Art

For this type of $NO_x$ sensor, the present applicant has previously proposed a semiconductor-type $NO_x$ sensor made using β-type $Nb_2O_5$ having a high sensitivity to $NO_x$ in an exhaust gas (see Japanese Patent Application Laid-open No.8-15199).

The measurement of a concentration of $NO_x$ by the $NO_x$ sensor is carried out in the follower manner: If $NO_x$ is adsorbed onto the surface of a β-type $Nb_2O_5$ layer, the $NO_x$ exhibits an electron attracting effect, thereby causing an electron which is a carrier of the β-type $Nb_2O_5$ (an n-type semiconductor) to be attracted to and restricted in $NO_x$ and hence, the electric resistance value (which will be referred to as a resistance value hereinafter) of the β-type $Nb_2O_5$ layer is increased. This resistance value is converted into a concentration of $NO_x$ concentration.

The present inventors have made various researches about the $NO_x$ sensor and as a result, they have made clear the existance of the following improving points.

(a) To allow the $NO_x$ sensor to effectively function in an exhaust gas from an automobile vehicle, it is necessary to enhance the $NO_x$ sensitivity of the $NO_x$ sensor, so that the latter has a high ratio of S/N (S represents a signal, and N represents a noise).

(b) The $NO_x$ sensor shows a relatively high sensitivity not only to $NO_x$ in an exhaust gas, but also to $O_2$ and hence, in order to enhance the $NO_x$ sensitivity, it is necessary to reduce the $O_2$ sensitivity.

SUMMARY OF THE INVENTION

Accordingly, it is an object of the present invention to provide an $NO_x$ sensor of the above-described type for an exhaust gas, wherein the $NO_x$ sensitivity is further enhanced by controlling the crystal structure of β-type $Nb_2O_5$.

To achieve the above object, according to the present invention, there is provided an $NO_x$ sensor for an exhaust gas, which is made by sintering a plurality of columnar crystals of β-type $Nb_2O_5$, an average value M of aspect ratios b/a (wherein a represents a width and b represents a length) in the columnar crystals being in a range of $2.11 < M \leq 5$.

The columnar crystal of β-type $Nb_2O_5$ has a nature that the degree of increase in length b at a growth stage is larger than the degree of increase in width a. Therefore, the columnar crystal having a larger aspect ratio b/a has a length b larger than that of the columnar crystal having a smaller aspect ratio b/a.

Therefore, if the average value M of the aspect ratios b/a is set in the above range, the length b of the columnar crystal is increased more than that in a case where $M \leq 2.11$. Thus, in the adjacent columnar crystals, a relatively long gas passage is defined between crystals in a zone where they are not sintered to each other and hence, the $NO_x$-adsorbable area of the $NO_x$ sensor is increased. On the other hand, in a zone where the columnar crystals have been sintered to each other, the bonded area is increased, thereby permitting the movement of electrons between the adjacent columnar crystals to be performed smoothly. Thus, the $NO_x$ sensor exhibits a high $NO_x$ sensitivity.

The increase in bonded area as described above also is effective to enhance the strength of the $NO_x$ sensor.

However, if the average value M is in a range of $M \leq 2.11$, the degree of increase in length b of the columnar crystal is lower and hence, the bonded area is decreased. As a result, it is impossible to enhance the $NO_x$ sensitivity. On the other hand, the average value M larger than 5 means that the bonded area between the columnar crystals has been excessively increased, namely, the sintering of the $NO_x$ sensor has excessively advanced, thereby causing the $NO_x$ sensor to be increased in density. Therefore, when the $NO_x$ sensor has been bonded to a substrate simultaneously with the sintering, cracks, peeling-off or the like may be produced in the $NO_x$ sensor due to a difference in thermal expansion coefficient between the $NO_x$ sensor and the substrate.

It is another object of the present invention to provide an $NO_x$ sensor producing process of the above-described type, by which the $NO_x$ sensor can be mass-produced.

To achieve the above object, according to the present invention, there is provided a process for producing an $NO_x$ sensor for an exhaust gas, comprising the steps of subjecting a powder comprised of an aggregate of α-type $Nb_2O_5$ particles to a first heating treatment at a heating temperature $T_3$ set in a range of $600° C. \leq T_3 \leq 890° C.$, thereby producing the coalescence of the plurality of α-type $Nb_2O_5$ particles to produce a plurality of larger particles of α-type $Nb_2O_5$, subjecting the powder resulting from the first heating treatment to a second heating treatment at a heating temperature $T_4$ set in a range of $950° C. \leq T_4 \leq 1,200° C.$, thereby producing the transformation of the α-type $Nb_2O_5$ into β-type $Nb_2O_5$ and the coalescence of the larger particles to grow a plurality of columnar crystals of β-type $Nb_2O_5$, and sintering the columnar crystals.

A sufficient amount of larger particles having a required size can be produced by the first heating treatment. However, if the heating temperature $T_3$ is lower than $600° C.$, the coalescence of the plurality of α-type $Nb_2O_5$ particles is inactive and for this reason, it is impossible to produce a sufficient amount of larger particles. On the other hand, if $T_3 > 890° C.$, β-type $Nb_2O_5$ particles are produced by the transformation of α-type $Nb_2O_5$ and are difficult to be coalesced. For this reason, it is impossible to produce a sufficient amount of larger particles having a required size.

An $NO_x$ sensor having a configuration as described above is produced by the second heating treatment. However, if the heating temperature $T_4$ is lower than $950° C.$, the coalescence of the larger particles is inactive, resulting in an average value M in a range of $M \leq 2.11$, causing the above-described disadvantages to occur. On the other hand, if $T_4 > 1,200° C.$, the coalescence is excessively conducted, resulting in an average value M larger than 5. Therefore, when the resulting $NO_x$ sensor is bonded to a substrate by the second heating treatment, there is encountered a disadvantage that the $NO_x$ sensor is peeled off from the substrate, or cracked.

Further, it is an object of the present invention to provide an $NO_x$ sensor for an exhaust gas, which has a high sensitivity to $NO_x$ in an exhaust gas and a lower sensitivity to $O_2$ and which is excellent in practical use.

To achieve the above object, according to the present invention, an $NO_x$ sensor for an exhaust gas, having the above-described configuration, includes $TiO_2$ in a content of $0.1\%$ by weight $\leq TiO_2 \leq 20\%$ by weight.

If the $NO_x$ sensor is formed in such configuration, the sensitivity of the $NO_x$ sensor to $NO_x$ can be further enhanced, and the sensitivity to $O_2$ can be lowered.

It is believed that this is due to the following reason:

If a particular amount of $TiO_2$ is contained in the β-type $Nb_2O_5$ layer, predetermined amount of $TiO_2$ is exposed to the surface of the β-type $Nb_2O_5$ layer to exist in a dotted manner on the surface. Thus, $NO_x$ in an exhaust gas is efficiently adsorbed to $TiO_2$ and overflows from $TiO_2$, namely, a spill-over phenomenon occurs. The overflowing $NO_x$ is adsorbed to the surface of β-type $Nb_2O_5$.

The amount of $NO_x$ in the exhaust gas has been adsorbed on the surface of the β-type $Nb_2O_5$ layer by its own effect, and the amount of $NO_x$ adsorbed by the spill-over phenomenon is added to the amount of $NO_x$ previously adsorbed. Therefore, the amount of $NO_x$ adsorbed is remarkably increased, as compared with the $NO_x$ sensor made using only β-type $Nb_2O_5$. If the $NO_x$ sensor is made using $TiO_2$ in combination with β-type $Nb_2O_5$ in the above manner, the sensitivity of the $NO_x$ sensor to $NO_x$ is higher.

On the other hand, $O_2$ in the exhaust gas is adsorbed intrinsically at a certain proportion on the surface of the β-type $Nb_2O_5$ layer, but the site of $O_2$ adsorbed is occupied by $NO_x$ by the spill-over phenomenon. Therefore, the amount of $O_2$ adsorbed on the surface of the β-type $Nb_2O_5$ layer is decreased, as compared with the $NO_x$ sensor made using only β-type $Nb_2O_5$. If the $NO_x$ sensor is made using $TiO_2$ in combination with β-type $Nb_2O_5$ in the above manner, the sensitivity of the $NO_x$ sensor to $O_2$ is lowered.

In this case, predetermined amount of $TiO_2$ exists in the β-type $Nb_2O_5$ layer and hence, in measuring a concentration of $NO_x$, the $TiO_2$ does not participate in the change in resistance value of the β-type $Nb_2O_5$ layer.

However, if the content of $TiO_2$ is lower than 0.1% by weight, or higher than 20% by weight, the sensitivity of the $NO_x$ sensor to $NO_x$ is lowered, while the sensitivity to $O_2$ is increased.

The $NO_x$ sensor has a nature that if the exhaust gas concentration is lowered, the amount of $NO_x$, $O_2$ and the like adsorbed is decreased, and if the temperature of the exhaust gas is lowered, the amount of $NO_x$, $O_2$ and the like adsorbed is increased.

The above and other objects, features and advantages of the invention will become apparent from the following description of the preferred embodiment taken in conjunction with the accompanying drawings.

BRIEF DESCRIPTION OF THE DRAWINGS

FIG. 9 is a plan view of a second example of an $NO_x$ measuring element;

DETAILED DESCRIPTION OF THE PREFERRED EMBODIMENTS

Figure 1:
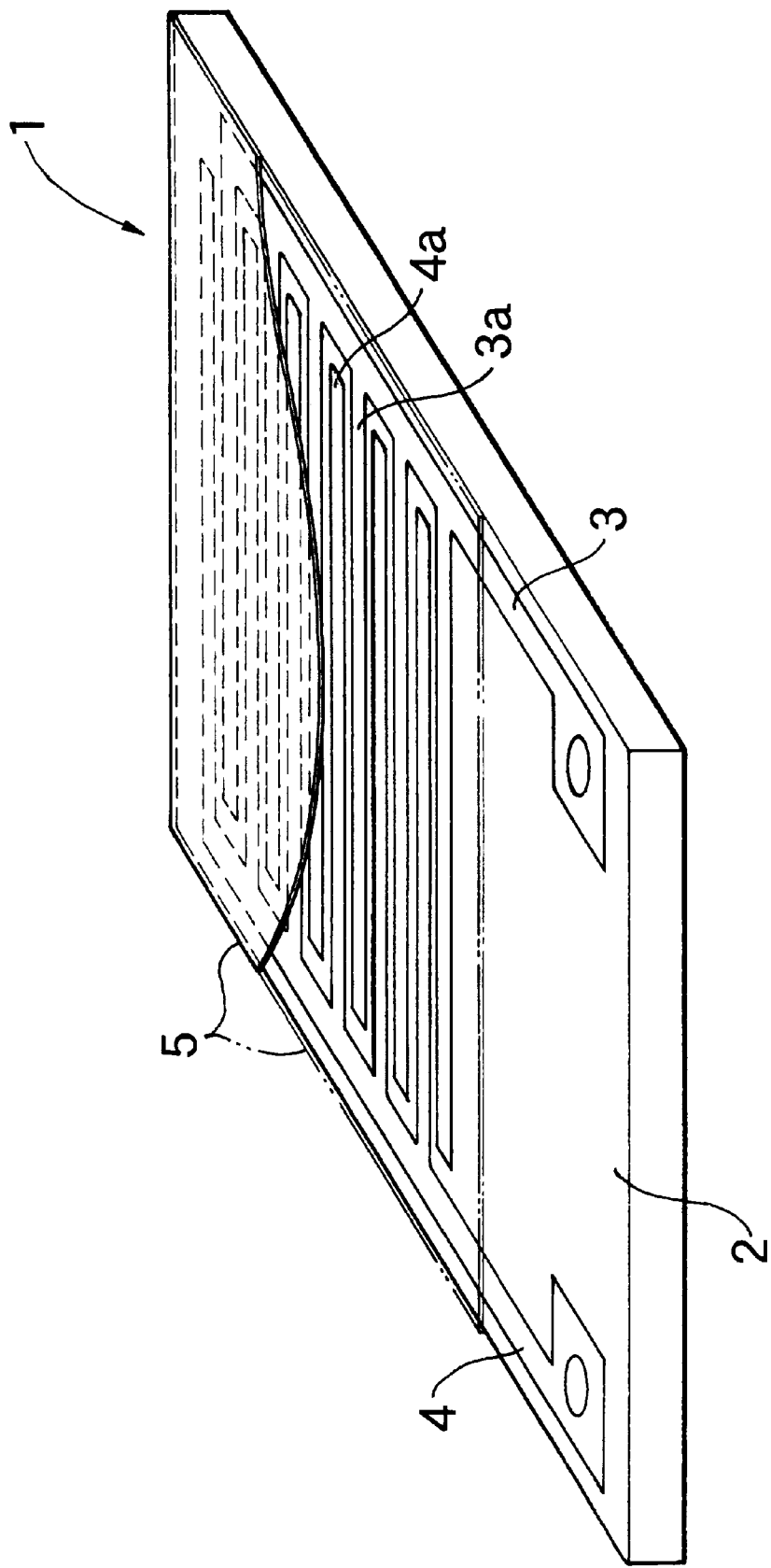
FIG. 1 is a perspective view of a first example of an $NO_x$ measuring element of the present invention.

Referring to FIG. 1, an $NO_x$ measuring element 1 is comprised of a substrate 2 made of $Al_2O_3$, a pair of thin film-shaped electrodes 3 and 4 made of Pt, which have comb-shaped portions 3a and 4a disposed thereon, so that they are meshed with each other, and which are adhered to a surface of the substrate 2, and a thin film-shaped semiconductor $NO_x$ sensor 5 having a thickness of 10 to 20 μm and adhered to the comb-shaped portions 3a and 4a and the substrate 2 to cover the comb-shaped portions 3a and 4a. A heater is mounted on a back of the substrate 2. The electrodes 3 and 4 are connected to a power source through a multi-meter.

Figure 2:
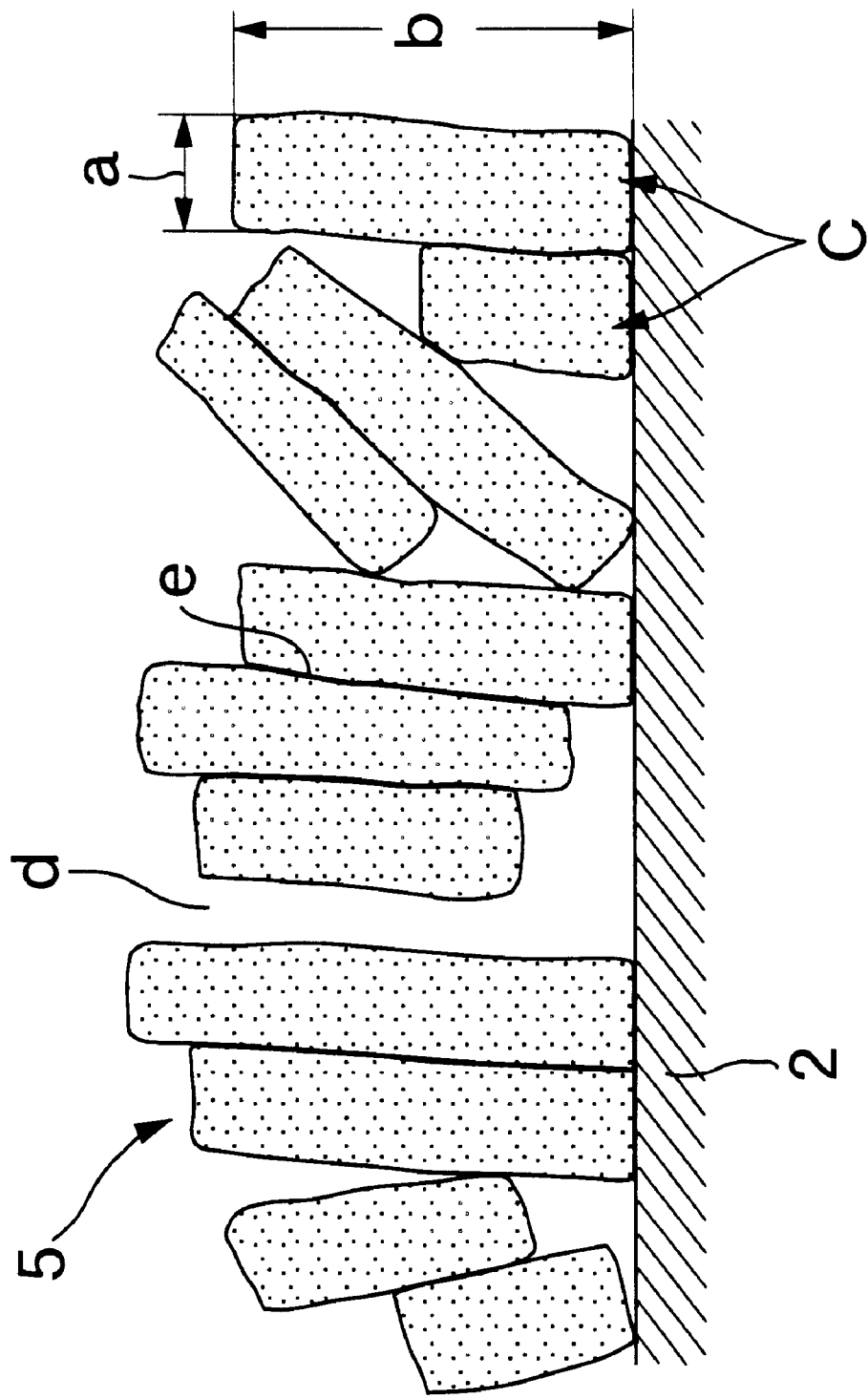
FIG. 2 is an illustration of a crystal structure of an $NO_x$ sensor of the present invention.

As shown in FIG. 2, an $NO_x$ sensor 5 is produced by sintering a plurality of columnar crystals C of β-type $Nb_2O_5$, and the average value M of aspect ratios b/a (wherein a represents a width, and b represents a length) in the columnar crystals C is set in a range of $2.11 < M \leq 5$.

The columnar crystal C of β-type $Nb_2O_5$ has a nature that the degree of increase in length b at the stage of growth thereof is larger than the degree of increase in width a. Therefore, the columnar crystal C having a larger aspect ratio b/a has a length b larger than that of the columnar crystal C having a smaller aspect b/a.

If the average value M of the aspect ratios b/a is set in the above-described range, the length b of the columnar crystal C is increased more than that of columnar crystal C having an average value $M \leq 2.11$. Therefore, for the adjacent columnar crystals, a relatively long gas passage d is defined between them in a zone where they have not been sintered with each other and hence, the $NO_x$-absorbable area of the $NO_x$ sensor 5 is increased. On the other hand, the bonded area is increased in a zone e where the adjacent columnar crystals C have been sintered with each other, so that the movement of electrons between the adjacent columnar crystals C is smoothly conducted. Thus, the $NO_x$ sensor 5 exhibits a high sensitivity to $NO_x$.

The increase in bonded area as described above is effective to enhance the strength of the $NO_x$ sensor 5.

Figure 3:
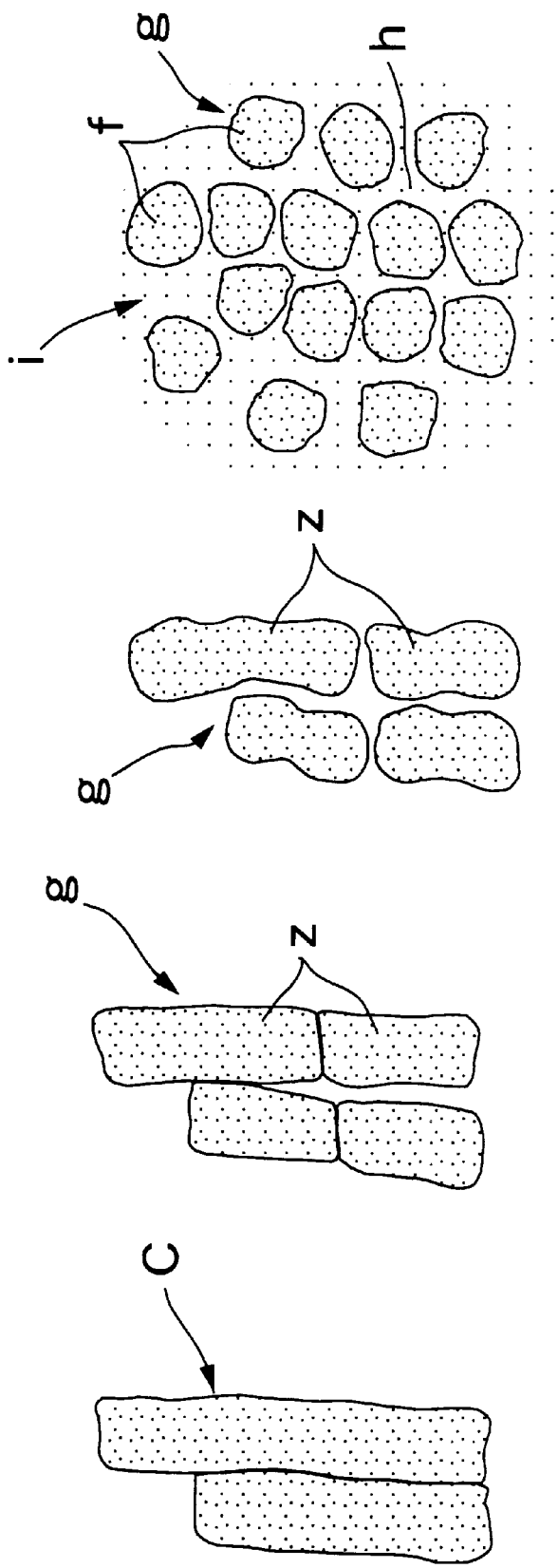
FIGS. 3A to 3D are illustrations for explaining a process for forming columnar crystals of β-type $Nb_2O_5$.

The $NO_x$ sensor 5 is produced in the following manner:

(1) As shown in FIG. 3A, a printing paste i including a powder g which is an aggregate of α-type $Nb_2O_5$ particles f and a binder solution h comprised of a binder and an organic solvent is applied onto the substrate 2 having the pair of electrodes 3 and 4 to cover the comb-shaped portions 3a and 4a, thereby forming a thin film.

Figure 4:
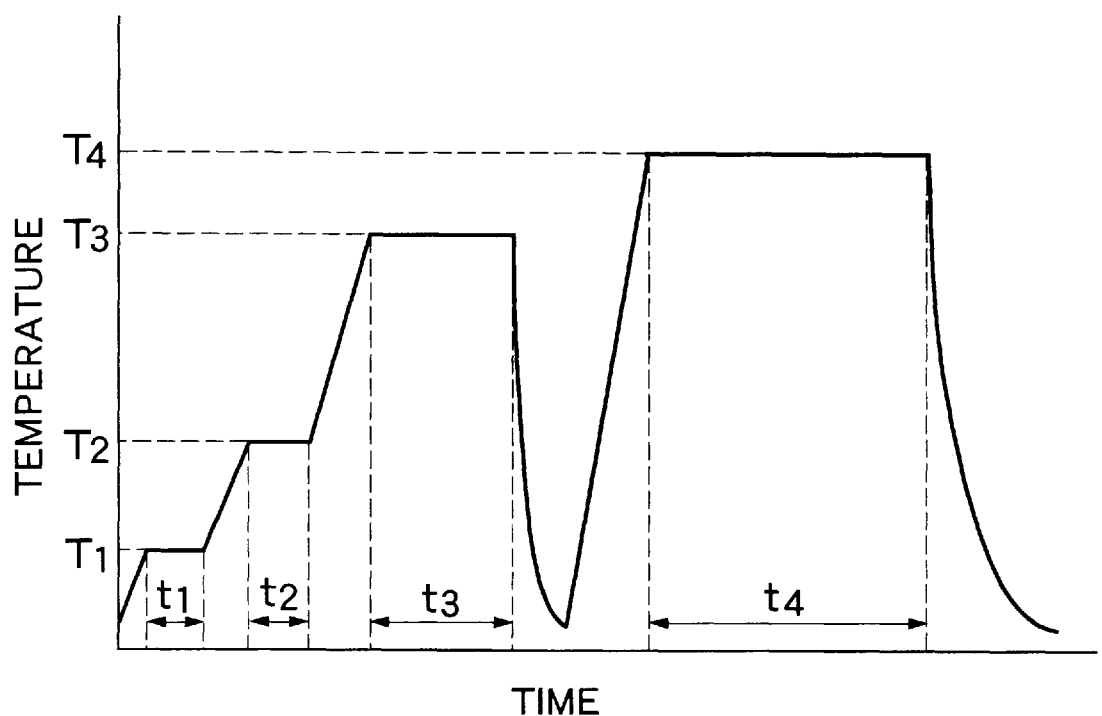
FIG. 4 is a graph illustrating the relationship between the time and the temperature in a heating treatment.

(2) As shown in FIG. 4, the thin film is subjected to a primary heating treatment at a heating temperature $T_1$ set in a range of $100°C. \leq T_1 \leq 200°C.$ for a heating time $t_1$ set in a range of $t_1 \geq 10$ minutes, and the organic solvent in the binder solution h is removed. In this case, if the heating temperature $T_1$ is lower than $100°$ C., or if the heating time $t_1$ is shorter than 10 minutes, the removal of the organic solvent cannot be sufficiently performed. On the other hand, if $T_1 > 200°$ C., the organic solvent is rapidly evaporated to create air voids in the thin film, and as a result the produced $NO_x$ sensor has a reduced quality.

(3) As shown in FIG. 4, the thin film Is subjected to a secondary heating treatment at a heating temperature $T_2$ set in a range of $370°C. \leq T_2 \leq 470°C.$ for a heating time $t_2$ set in a range of $t_2 \geq 10$ minutes to decompose the binder. In this case, if the heating temperature $T_2$ is lower than $370°$ C., or if the heating time $t_2$ is shorter than 10 minutes, the decomposition of the binder cannot be sufficiently performed. On the other hand, if $T_2 > 470°$ C., the binder is rapidly decomposed to produce air voids in the thin film by the decomposition gas and as a result, the produced $NO_x$ sensor 5 has a reduced quality.

(4) As shown in FIG. 4, the powder g which is the aggregate of α-type $Nb_2O_5$ particles f is subjected to a tertiary heating treatment (a first heating treatment) at a heating temperature $T_3$ set in a range of $600°C. \leq T_3 \leq 890°C.$ for a heating time $t_3$ set in a range of $t_3 \geq 30$ minutes. This produces the coalescence of the plurality of α-type $Nb_2O_5$ particles f to produce a plurality of larger particles z of α-type $Nb_2O_5$, as shown in FIG. 3B. The reason why the heating temperature $T_3$ is set in the above-described range is as described above. If the heating time $t_3$ is shorter than 30 minutes, it is impossible to produce a sufficient amount of larger particles z.

(5) As shown in FIG. 4, after the tertiary heating treatment, the powder g and the substrate 2 are gradually cooled down to substantially room temperature, whereby the thermal stresses thereof are moderated, as shown in FIG. 3C.

(6) As shown in FIG. 4, the powder g is subjected to a quartic heating treatment (a second heating treatment) at a heating temperature $T_4$ set in a range of $950°C. \leq T_4 \leq 1,200°C.$ for a heating time $t_4$ set in a range of $t_4 \geq 1$ hour. This causes the transformation of α-type $Nb_2O_5$ into β-type $Nb_2O_5$ and the coalescence of the plurality of larger particles j to produce a plurality of columnar crystals C of β-type $Nb_2O_5$ and to sinter the columnar crystals, as shown in FIG. 3D. The $NO_x$ sensor produced in the above manner is bound to the substrate 2 during the sintering course. The reason why the heating temperature $T_4$ is set in such range is as described above. If the heating time $t_4$ is shorter than 1 hour, it is impossible to sufficiently generate the above-described phenomenon.

EXAMPLE I

A. Production of $NO_x$ Sensor and $NO_x$ Measuring Element (1) A dispersion liquid comprised of a powder g (made by Soekawa Chemicals Co. Ltd.) which is an aggregate of α-type $Nb_2O_5$ particles f and the same amount of ethanol as the amount of the powder g was placed in a planetary ball mill, where it was mixed and pulverized. Then, the mixed/pulverized material was subjected to a drying treatment at $150°$ C. for 2 hours to produce a powder g having an average particle size of 0.2 μm.

(2) A mixture of the powder g and a solution of ethyl cellulose in α-terpineol (a binder solution h) was placed in the roll mill, where it was kneaded, thereby providing a printing paste i having a viscosity of about 100 Pa s.

(3) Likewise, using the printing paste i, a screen printing was carried out on the substrate 2 to cover the comb-shaped portions 3a and 4a, thereby forming a thin film. Then, the thin film was left to stand for approximately 24 hours.

(4) A plurality of specimens each having a thin film formed on a substrate were produced in the same manner.

(5) Each of the thin films was subjected to all or selected one or more of primary to quartic heating treatments to produce an $NO_x$ sensor 5 and the $NO_x$ sensor 5 is sintered to the substrate 2, thereby providing an $NO_x$ measuring element 1.

Table 1 shows conditions for the heating treatments for examples 1 to 3 and comparative examples 1 to 7 of $NO_x$ sensors 5. In each example, the thickness of the $NO_x$ sensor 5 was of 20 μm.

TABLE 1

| | Heating treatment condition ||||||||
| | Primary || Secondary || Tertiary || Quartic ||
| $NO_x$ sensor | Heating temperature $T_1$ (° C.) | Heating Time $t_1$ (minutes) | Heating temperature $T_2$ (° C.) | Heating time $t_2$ (minutes) | Heating temperature $T_3$ (° C.) | Heating time $t_3$ (minutes) | Heating temperature $T_4$ (° C.) | Heating time $t_4$ (minutes) |
|---|---|---|---|---|---|---|---|---|
| Example | | | | | | | | |
| 1 | 100 | 30 | 450 | 30 | 870 | 120 | 1100 | 240 |
| 2 | 150 | | 400 | | 800 | | 1000 | |
| 3 | 150 | | 400 | | 820 | | 960 | |
| Comparative Example | | | | | | | | |
| 1 | 100 | 30 | 450 | 30 | 820 | 120 | 1320 | 240 |
| 2 | 200 | | 350 | | 820 | | 1250 | |
| 3 | 150 | | 400 | | — | — | 1100 | |

TABLE 1-continued

| | Heating treatment condition | | | | | | | |
|---|---|---|---|---|---|---|---|---|
| | Primary | | Secondary | | Tertiary | | Quartic | |
| $NO_x$ sensor | Heating temperature $T_1$ (° C.) | Heating Time $t_1$ (minutes) | Heating temperature $T_2$ (° C.) | Heating time $t_2$ (minutes) | Heating temperature $T_3$ (° C.) | Heating time $t_3$ (minutes) | Heating temperature $T_4$ (° C.) | Heating time $t_4$ (minutes) |
| 4 | 150 | | 400 | | — | | 800 | |
| 5 | 150 | | 400 | | 800 | 120 | 920 | |
| 6 | 150 | | 400 | | 800 | | 900 | |
| 7 | 150 | | 400 | | 950 | | 1000 | |

B. Calculation of Average Value M of Aspect Ratios b/a

The photomicrograph of 3,000 magnification was taken of vertical sections of the examples 1 to 3 and the comparative examples 1 to 7. An area of 50 mm square in each of the photomicrographs was arbitrarily selected, and 20 columnar crystals C were selected from a large number of columnar crystals C existing in such area. Aspect ratios b/a of these selected columnar crystals C were determined, and an average value M was calculated from the aspect ratios b/a. In this case, the width a of the columnar crystal C is an average value determined from the maximum and minimum values thereof. The same is true of the length b. The average M of the aspect ratios b/a will be described later.

C. Measurement of $NO_x$ Sensitivity of $NO_x$ Sensor

Table 2 shows the compositions of first and second gases used for the measurement of the sensitivity to $NO_x$ (in this case, NO and so forth).

Table 2 shows compositions of the first gas and the second gas used for measuring the sensitivity to $NO_x$ which is NO in this case and hereinafter.

TABLE 2

| | First gas | Second gas |
|---|---|---|
| $O_2$ | | 0.2% by volume |
| $CO_2$ | | 14% by volume |
| CO | | 20 ppm |
| $CH_4$ | | 70 ppm |
| $H_2O$ | | 10% by volume |
| $NO_x$ | 12 ppm | 96 ppm |
| $N_2$ | | Balance |

In measuring the sensitivity to $NO_x$, the $NO_x$ measuring element 1 having a temperature of 300° C. was first placed into the first gas having a temperature set at 150° C. and a gas flow rate set at 2000 cc/min, and a resistance value $R_1$ was measured. Then, the $NO_x$ measuring element 1 having the same temperature was placed into the second gas having a temperature and a gas flow rate set at the same values as those described above, and a resistance value $R_2$ was measured.

Thereafter, an $NO_x$ sensitivity (%) was calculated using the following equation:

$$NO_x \text{sensitivity} = \{(R_2 - R_1)/R_1\} \times 100$$

Table 3 shows the relationship between the average value M of the aspect ratios b/a of the columnar crystals C and the $NO_x$ sensitivity for the examples 1 to 3 and the comparative examples 1 to 7. In the case of the comparative example 1, the $NO_x$ sensor 5 was largely peeled off from the substrate 2 and was largely cracked and hence, it was impossible to measure the $NO_x$ sensitivity.

TABLE 3

| | Average value M of aspect ratios b/a | $NO_x$ sensitivity (%) |
|---|---|---|
| Example | | |
| 1 | 4.12 | 76 |
| 2 | 3.81 | 85 |
| 3 | 3.10 | 80 |
| Comparative Example | | |
| 1 | 6.20 | — |
| 2 | 5.48 | 80 |
| 3 | 2.11 | 58 |
| 4 | 1.70 | 44 |
| 5 | 1.68 | 42 |
| 6 | 1.27 | 40 |
| 7 | 1.20 | 35 |

Figure 5:
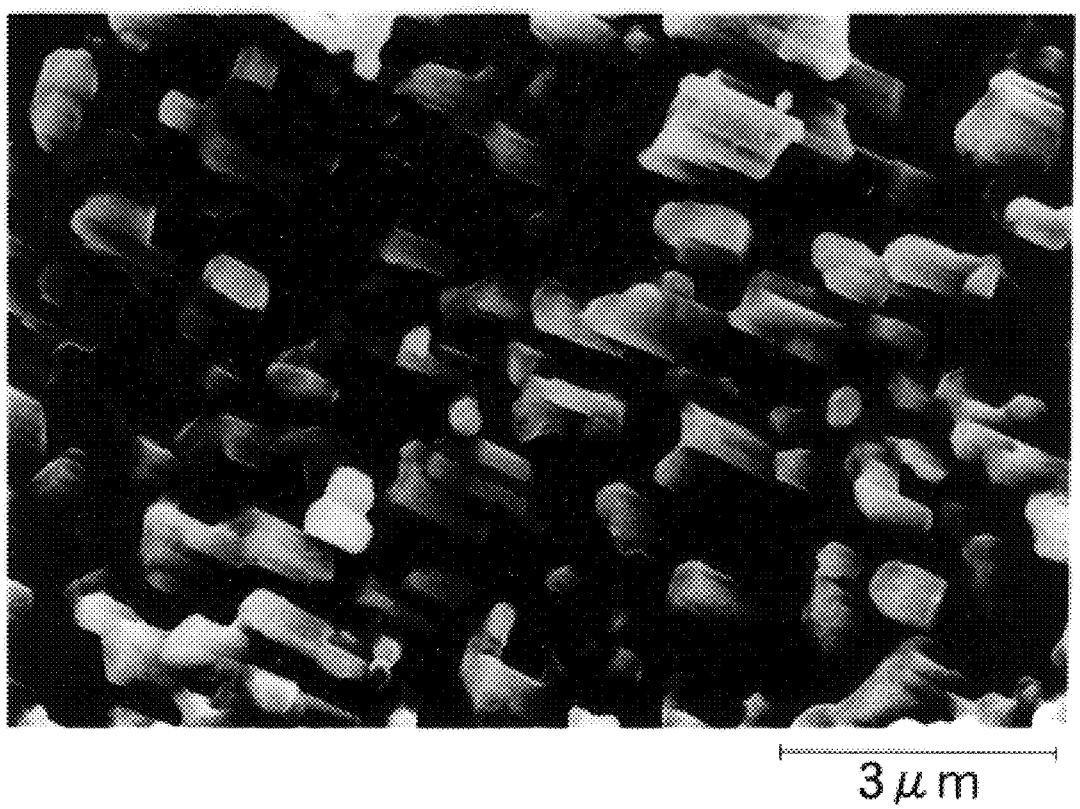
FIG. 5 is a photomicrograph showing shapes of crystals in example 2 of the $NO_x$ sensor.
Figure 6:
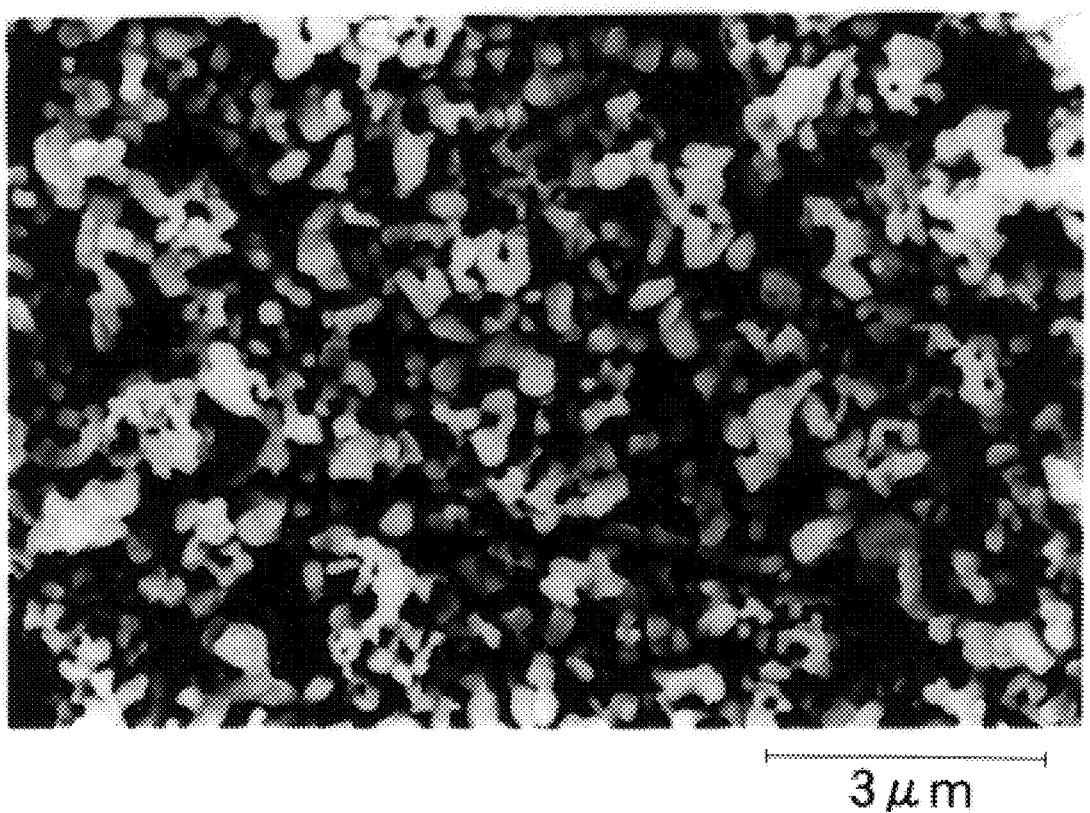
FIG. 6 is a photomicrograph showing shapes of crystals in example 4 of the $NO_x$ sensor.

FIG. 5 is a photomicrograph showing the crystal shape of the example 2, and FIG. 6 is a photomicrograph showing the crystal shape of the comparative example 4. It can be seen that the length b and aspect ratio b/a of the columnar crystals C in the example 2 are larger than those in the comparative example 4.

Figure 7:
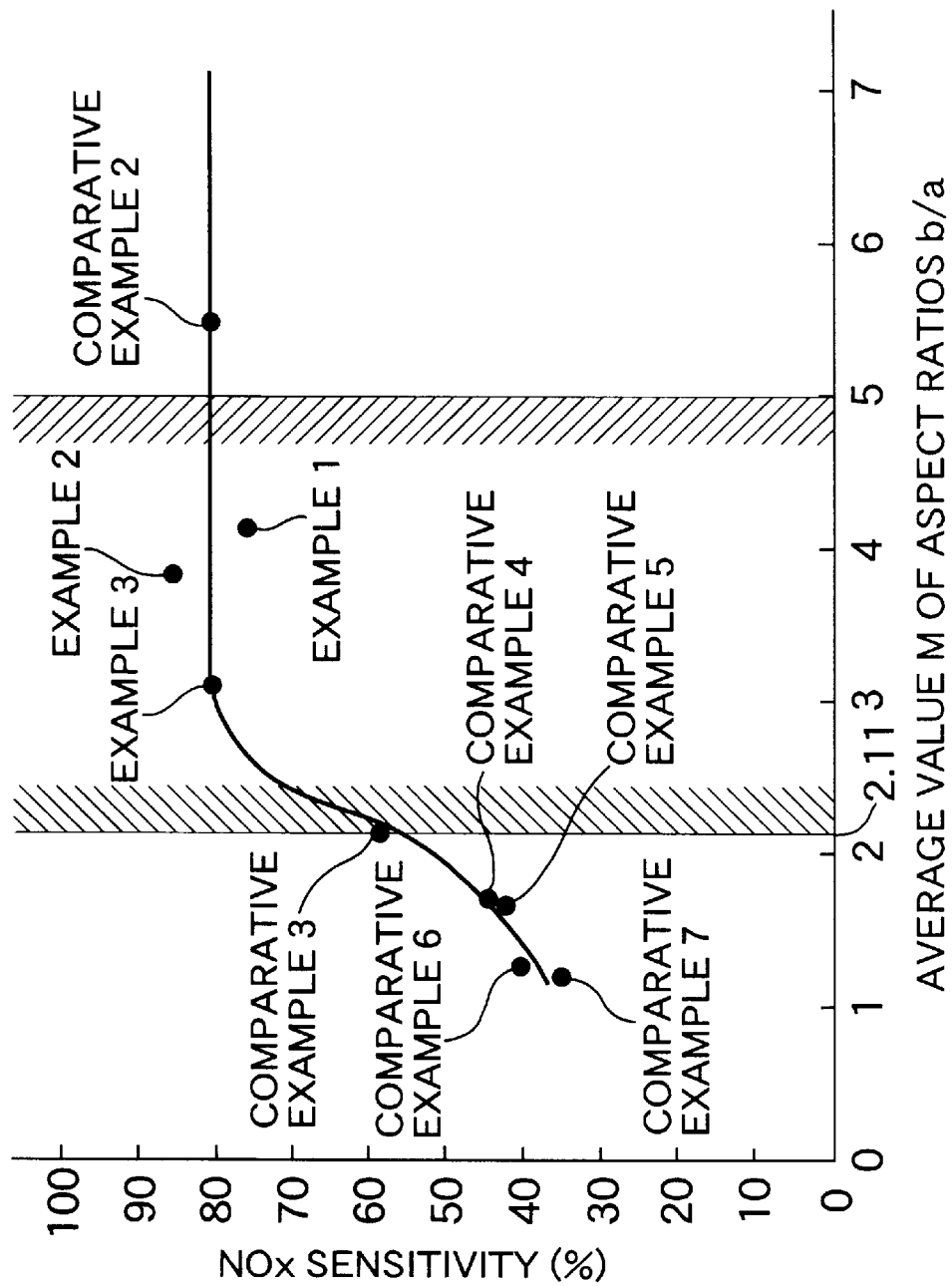
FIG. 7 is a graph illustrating the relationship between the average value M of aspect ratios b/a and the sensitivity to $NO_x$.

FIG. 7 is a graph taken from Table 3. In FIG. 7, a change point appears at a location of the comparative example 3. Therefore, the $NO_x$ sensitivity can be enhanced to 60% or more by setting the average value M of the aspect ratios b/a in a range of b/a>2.11. In the case of the comparative example 2 having the average value M of the aspect ratios b/a equal to 5.48, a portion of the $NO_x$ sensor 5 was peeled off from the substrate 2.

D. Measurement of Reject Rate

The 20 $NO_x$ measuring elements in each of the examples 1 to 3 and the comparative examples 1 to 7 made through the producing steps were left to stand at room temperature for 3 days. Then, the presence or absence of the peel-off of the $NO_x$ sensor 5 from the substrate 2 and the cracks of the $NO_x$ sensor 5 was visually examined for the example 1 and the like. The $NO_x$ measuring elements with the $NO_x$ sensor 5 peeled off or cracked were determined as reject articles, and the reject rate of them was calculated. Table 4 shows the relationship between the average value M of the aspect ratios b/a and the reject rate in the examples 1 to 3 and the comparative examples 1 to 7.

TABLE 4

| | Average value M of aspect ratios b/a | Reject rate (%) |
|---|---|---|
| Example | | |
| 1 | 4.12 | 5 |
| 2 | 3.81 | 0 |
| 3 | 3.10 | 5 |
| Comparative Example | | |
| 1 | 6.20 | 70 |
| 2 | 5.48 | 25 |
| 3 | 2.11 | 0 |
| 4 | 1.70 | 5 |
| 5 | 1.68 | 0 |
| 6 | 1.27 | 5 |
| 7 | 1.20 | 0 |

Figure 8:
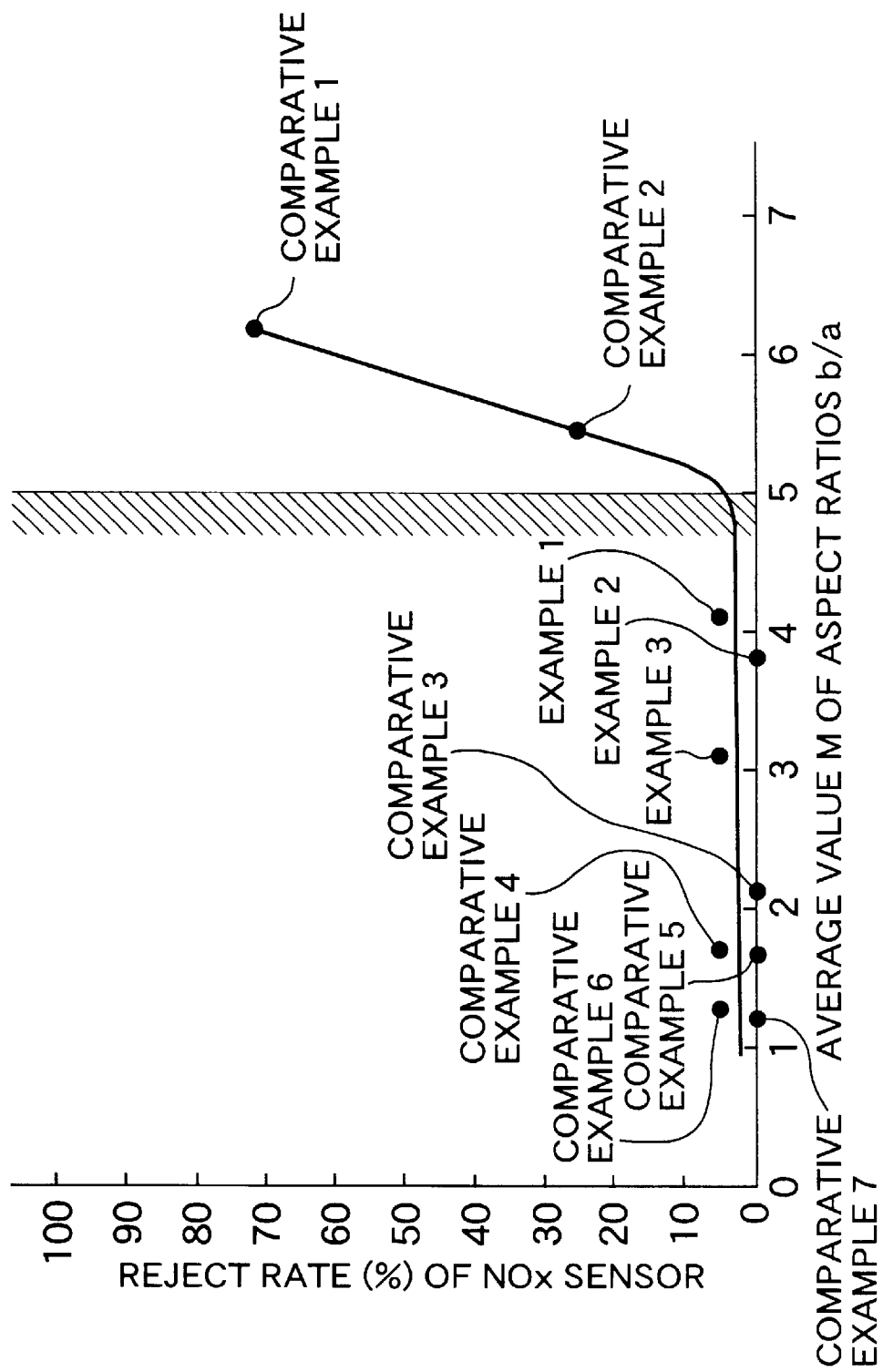
FIG. 8 is a graph illustrating the relationship between the average value M of aspect ratios b/a and the reject rate of the $NO_x$ sensor.

FIG. 8 is a graph taken from Table 4. It can be seen from FIG. 8 that if the average value M of the aspect ratios b/a is set in a range of $M \leq 5$, the reject rate is extremely decreased.

E. Correction of Output from $NO_x$ Measuring Element $\beta$-type $Nb_2O_5$ forming the $NO_x$ sensor 5 is a semiconductor and hence, if the temperature thereof is changed, the resistance value is changed. For this reason, an error is produced in the output from the $NO_x$ measuring element 1.

An $NO_x$ measuring element 1 shown in FIG. 9 has been developed for the purpose of correcting the error. This $NO_x$ measuring element 1 includes an $NO_x$ measuring element region K having a structure similar to that described above, and a correcting thermistor region L.

The correcting thermistor region L is comprised of a substrate 2 made of $Al_2O_3$, which is common to the $NO_x$ measuring element region K, a pair of thin film-shaped electrodes 4 and 13 which have comb-shaped portions 4b and 13a disposed thereon, so that they are meshed with each other, and which are adhered to a surface of the substrate 2, and a thin film-shaped thermistor m adhered to the comb-shaped portions 4b and 13a and the substrate 2 to cover the comb-shaped portions 4b and 13a. One, namely electrode 4, of the electrodes is common to the $NO_x$ measuring element region K. A heater is provided on a back of the substrate 2.

It is required for a material forming the thermistor m that the temperature factor thereof a resistor approximates that of the $NO_x$ sensor 5, and that the material does not have a sensitivity to $NO_x$. In this embodiment, because the temperature factor (B constant) of $\beta$-type $Nb_2O_5$ is of 4,800 K, $\alpha$-type $Fe_2O_3$ having a temperature factor of 4,700 K was used as a material forming the thermistor m. The thermistor region L was produced using the following process:

(1) An $\alpha$-type $Fe_2O_3$ powder was pulverized using a planetary ball mill.

(2) A mixture of the $\alpha$-type $Fe_2O_3$ powder and a solution of ethyl cellulose in $\alpha$-terpineol was placed in a roll mill, where it was kneaded, thereby providing a printing paste having a viscosity of about 100 Pa•s.

(3) As shown in FIG. 9, using the printing paste a screen printing was carried out on the substrate 2 having the pair of electrodes 4 and 13 to cover the comb-shaped portions 4b and 13a, thereby forming a thin film.

(4) The thin film was subjected to a heating treatment at 900° C. for one hour to sinter the $\alpha$-type $Fe_2O_3$ powder and to bind the $\alpha$-type $Fe_2O_3$ powder to the substrate 2, thereby producing a thermistor m.

Figure 10B:
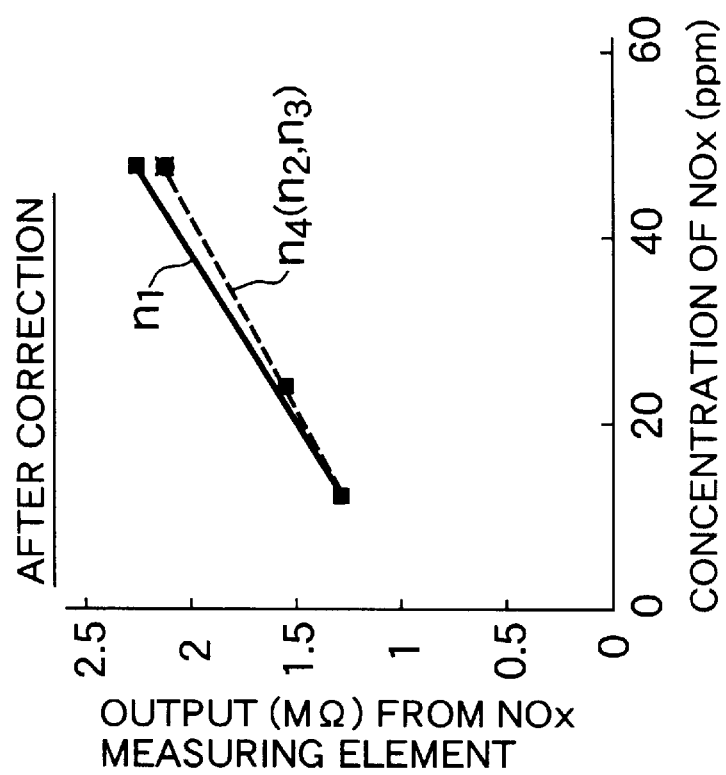
FIGS. 10A and 10B are graphs illustrating the concentration of $NO_x$ and the output from the $NO_x$ measuring element, with FIG. 10A corresponding to before correction and FIG. 10B corresponding to after correction.
Figure 10A:
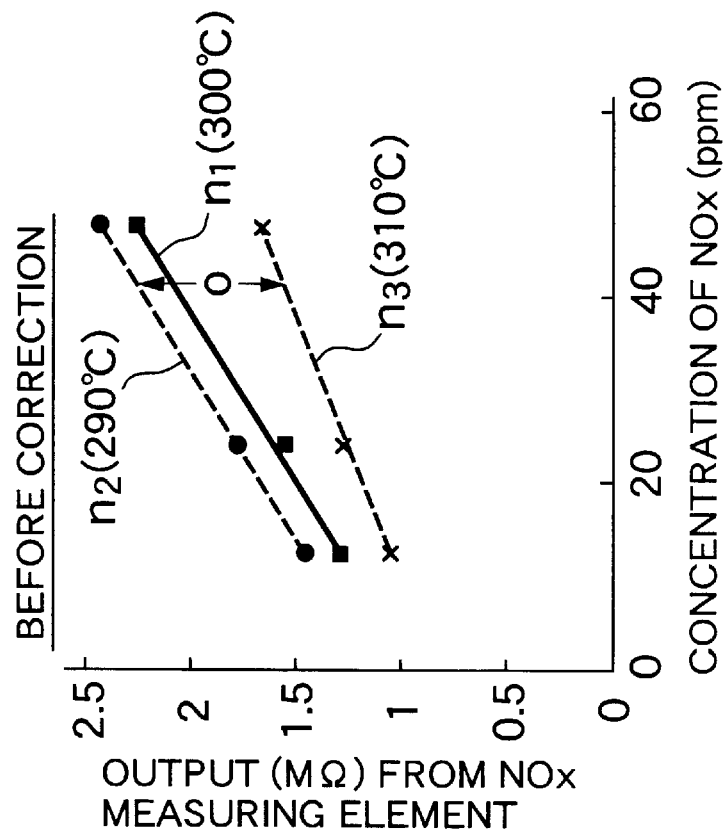

In the $NO_x$ measuring element 1 having the example 2 as the $NO_x$ sensor 5, if the temperature thereof is maintained constant at 300° C. and the concentration of $NO_x$ is gradually increased, the output from the $NO_x$ measuring element 1 is increased as shown by a line $n_1$ in FIG. 10A. However, if the temperature of the $NO_x$ measuring element 1 is lowered to 290° C., the output from the $NO_x$ measuring element 1 is larger than that at 300° C., as shown by a line $n_2$ in FIG. 10A. On the other hand, if the temperature of the $NO_x$ measuring element 1 is increased to 310° C., the output from the $NO_x$ measuring element 1 is smaller than that at 300° C., as shown by a line $n_3$ in FIG. 10A. As a result, with a change in temperature, an error o is produced at a distance between the line $n_2$ at 290° C. and the line $n_3$ at 310° C.

In order to correct the error o, the change in temperature of the $NO_x$ measuring element region K is measured in the thermistor region L, and a correcting output value corresponding to the amount of temperature changed is subtracted from the output from the $NO_x$ measuring element region K, when the temperature has been dropped to 290° C., or such correcting output value is added to the output from the $NO_x$ measuring element region K, when the temperature has been increased to 310° C.

If such a correction is performed, the output $n_4$, shown in FIG. 10B, from the $NO_x$ measuring element 1 can approximate the output provided when the temperature of the $NO_x$ measuring element 1 is maintained constant at 300° C. as shown by the line $n_1$, thereby providing substantially no error o.

F. Stabilization of Output Characteristic of $NO_x$ Measuring Element

The output characteristic of the $NO_x$ measuring element 1 is varied with the passage of time and stabilized after a lapse of a predetermined time. Therefore, the $NO_x$ measuring element 1 was subjected to an aging treatment in the following manner:

A gas consisting of 2% by volume of $O_2$, 720 ppm of CO, 300 ppm of $C_3H_6$, 100 ppm of $NO_x$, 10% by volume of $H_2O$ and the balance of $N_2$ was prepared as a treating gas. The $NO_x$ measuring element 1 having the example 2 as the $NO_x$ sensor 5 was placed in such treating gas and subjected to the aging treatment under conditions of an element temperature of 310° C., an atmosphere temperature of 300° C., a voltage of 5 V applied to the electrodes 3 and 4 and a treating time of 3 to 15 hours.

Figure 11:
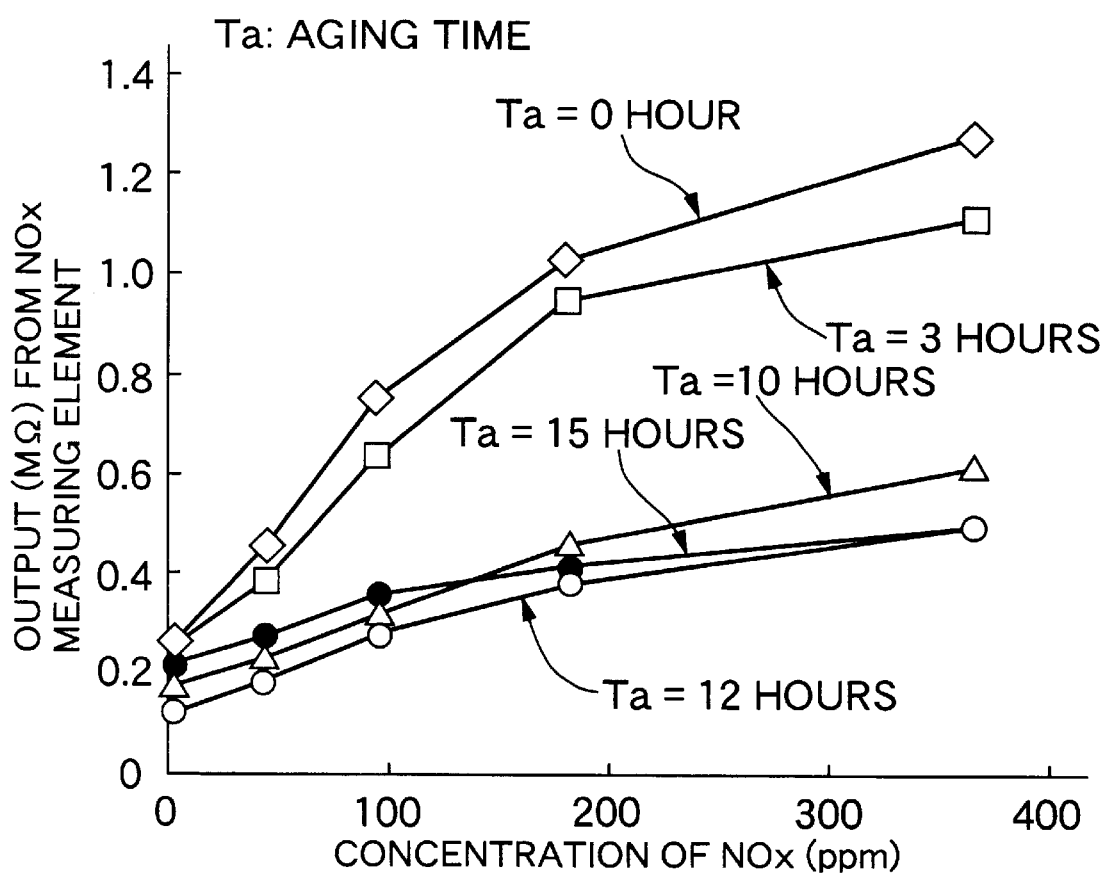
FIG. 11 is a graph illustrating the relationship between the concentration of $NO_x$ and the output from the $NO_x$ measuring element before and after aging.

FIG. 11 shows the relationship between the concentration of $NO_x$ and the output from the $NO_x$ measuring element 1 after a predetermined aging time Ta. It can be seen from FIG. 11 that if the aging treatment is conducted for 10 hours or more, the output from the $NO_x$ measuring element 1 is stabilized.

EXAMPLE II

An $NO_x$ measuring element 1 in EXAMPLE II has a structure similar to that shown in FIG. 1, except that an $NO_x$ sensor is formed of 99.5% by weight of $\beta$-$Nb_2O_5$ and 0.5% by weight of $TiO_2$.

Such an $NO_x$ measuring element 1 was produced using the following process:

(1) 50 Grams of dehydrated ethanol was added to 12.5 grams of niobium ethoxide [$Nb(OC_2H_5)_5$] (made by Soekawa Chemicals Co. Ltd.) and then, 74 mg of titanium ethoxide [$Ti(OC_2H_5)$] (made by Soekawa Chemicals Co. Ltd.) was added thereto to provide a mixture.

(2) 28 ml of Pure water was dropped into the mixture, while the mixture is being agitated, thereby providing a mixture comprised of oxides and hydroxides of niobium and titanium.

(3) The mixture was subjected to a drying treatment at 100° C. for 2 hours and then to a calcination at 500° C. for 30 minutes to provide an oxide mixture comprised of α-type $Nb_2O_5$ and 0.5% by weight of $TiO_2$.

(4) 60 Grams of the oxide mixture was mixed with 40 grams of a solution of ethyl cellulose in α-terpineol to provide a printing paste.

(5) Using the printing paste, a screen printing was carried out on a substrate 2 having a pair of electrodes 3 and 4 to cover both comb-shaped portions 3a and 4a to form a thin film.

(6) The substrate 2 having the thin film was subjected to a primary heating treatment at 150° C. for 30 minutes, a secondary heating treatment at 400° C. for 30 minutes, a tertiary heating treatment at 800° C. for 2 hours and a quartic heating treatment at 1,000° C. for 4 hours to produce an $NO_x$ measuring element 1 including an $NO_x$ sensor 5 formed of β-type $Nb_2O_5$ and $TiO_2$.

Then, various $NO_x$ measuring elements 1 including $NO_x$ sensors 5 with varied contents of $TiO_2$ were produced in the same manner as that described above.

Using, as a printing paste, a mixture of a powder which was an aggregate of 60 grams of α-type $Nb_2O_5$ particles resulting from the pulverization of α-type $Nb_2O_5$ having a purity of 99.9% (made by Soekawa Chemicals Co. Ltd.) in a planetary ball mill, and 40 grams of solution of ethyl cellulose in α-terpineol, a screen printing similar to that described above and a stepwise heating treatment were carried out to produce an $NO_x$ measuring element formed of β-type $Nb_2O_5$.

Figure 12:
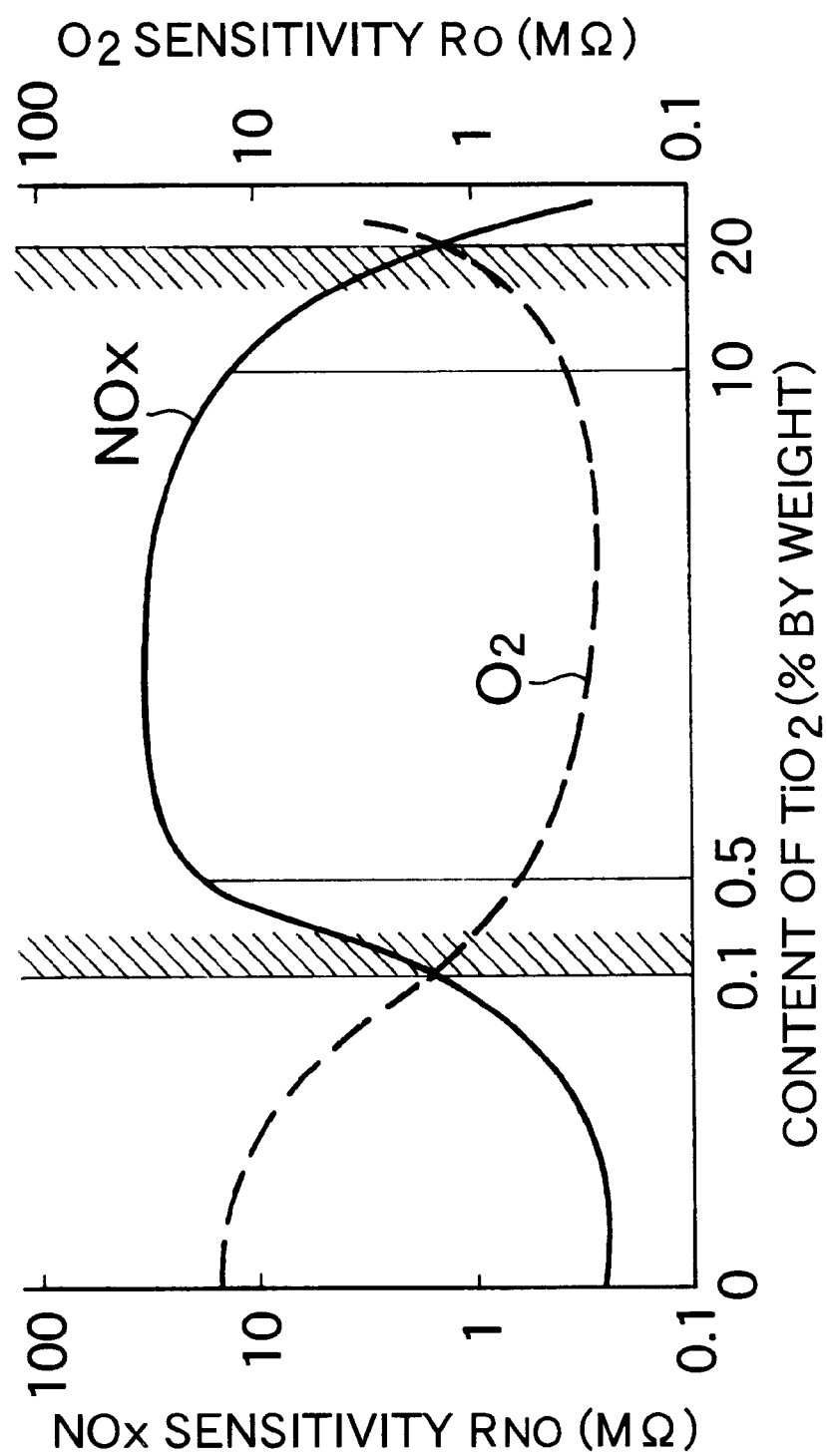
FIG. 12 is a graph illustrating the relationship between the content of $TiO_2$, the sensitivity $R_{NO}$ to $NO_x$ and the sensitivity $R_O$ to $O_2$.

Using the various $NO_x$ measuring elements, the sensitivities to $NO_x$ and $O_2$ were measured in the following manner:

First, the $NO_x$ measuring element 1 heated to 450° C. by a heater was placed into an atmosphere of nitrogen gas ($N_2$) having a temperature of 450° C., and an initial resistance $R_N$ was measured using a multi-meter. Then, the $NO_x$ measuring element 1 heated to 450° C. by the heater was placed into an atmosphere having a temperature of 450° C. and comprised of 1,000 ppm of $NO_x$ and the balance of $N_2$ as well as an atmosphere having a temperature of 450° C. and comprised of 2% by volume of $O_2$ and the balance of $N_2$, and a resistance value $R_{NO}$ in the atmosphere including $NO_x$ and a resistance value $R_O$ in the atmosphere including $O_2$ were measured using the multi-meter. FIG. 12 shows results of the measurement.

As is apparent from FIG. 12, if the content of $TiO_2$ is set in a range of 0.1% by weight $\leq TiO_2 \leq$ 20% by weight, the sensitivities $R_{NO}$ and $R_O$ to $NO_x$ and $O_2$ can be equivalent to each other, or the sensitivity $R_{NO}$ to $NO_x$ can be increased, and the sensitivity $R_O$ to $O_2$ can be reduced. Preferably, the content of $TiO_2$ is in a range of 0.5% by weight $\leq TiO_2 \leq$ 10% by weight. This ensures that the sensitivity $R_{NO}$ to $NO_x$ can be increased extremely, and the sensitivity $R_O$ to $O_2$ can be reduced extremely.

Then, first, second and third gases shown in Table 5 were prepared on the supposition of concentrations of $NO_x$, CO and HC (propylene) at an air/fuel ratio A/F equal to 22.

TABLE 5

| A/F = 22 | Constitution (ppm) | | | |
|---|---|---|---|---|
| | $NO_x$ | CO | HC | $N_2$ |
| First gas | 310 | — | — | Balance |
| Second gas | — | 900 | — | Balance |
| Third gas | — | — | 900 | Balance |

Figure 13:
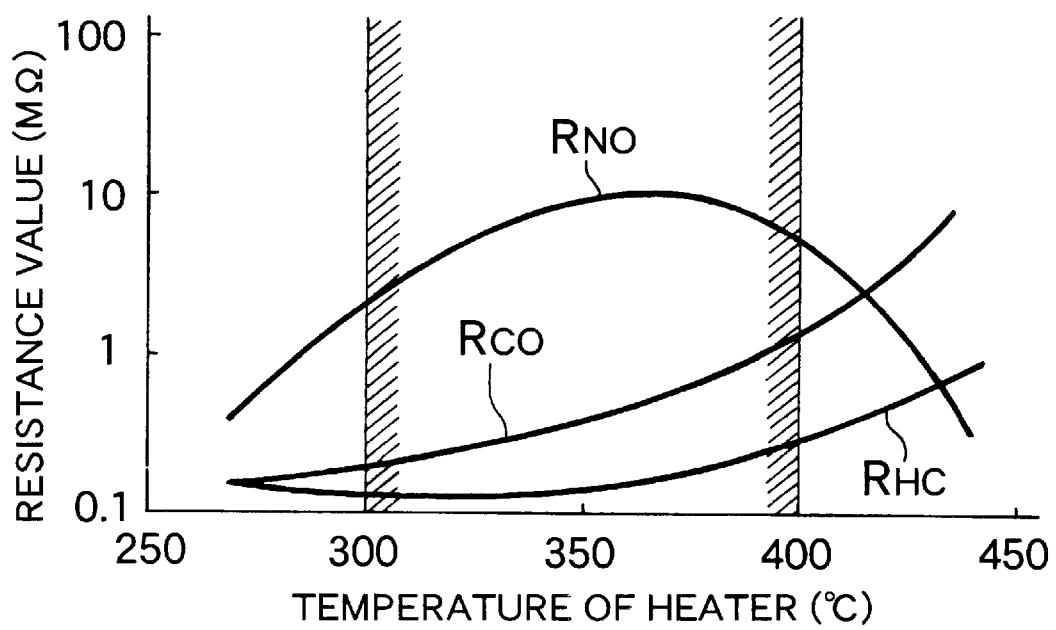
FIG. 13 is a graph illustrating the relationship between the heater temperature and the resistance value to various gases.

The $NO_x$ measuring element 1 including the $NO_x$ sensor 5 having a content of $TiO_2$ equal to 0.5% by weight was placed into each of the first, second and third gases maintained at respective temperatures, and sensitivities $R_{NO}$, $R_{CO}$ and $R_{HC}$ to $NO_x$, CO and HC were measured as resistance values to provide results shown in FIG. 13. In this case, the temperature of the $NO_x$ measuring element 1 heated by the heater was the same as the temperature of the gases.

As is apparent from FIG. 13, it can be seen that at the air/fuel ratio A/F equal to 22, the sensitivity $R_{NO}$ of the $NO_x$ sensor 5 to $NO_x$ is increased, while the sensitivities $R_{CO}$ and $R_{HC}$ of the $NO_x$ sensor 5 to CO and HC are reduced, by maintaining the heater temperature T in a range of 300° C. $\leq T \leq$ 400° C. Therefore, it is preferred that the heater temperature T is maintained in such range.

Figure 14:
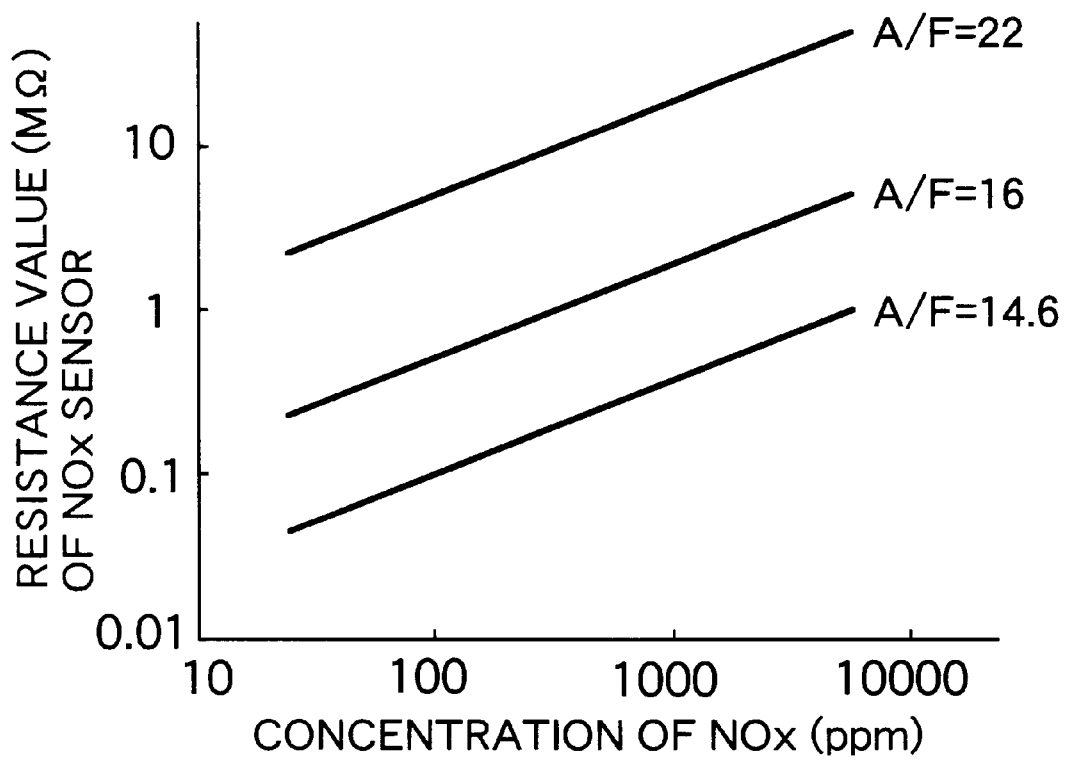
FIG. 14 is a graph illustrating the relationship between the concentration of $NO_x$ and the resistance value of the $NO_x$ sensor.

FIG. 14 shows the relationship between the concentration of $NO_x$ and the resistance value of the $NO_x$ sensor 5 at air/fuel ratios equal to 14.6, 16 and 22. Table 6 shows the relationship between the air/fuel ratio and the concentration of $O_2$ (a general value).

TABLE 6

| Air/fuel ratio A/F | 14.6 | 16 | 18 | 22 |
|---|---|---|---|---|
| Concentration of $O_2$ (% by volume) | 0.5 | 1.9 | 4.3 | 8.0 |

As is apparent from FIG. 14 and Table 6, if the concentration of $NO_x$ is increased, the resistance value of the $NO_x$ sensor 5 is increased by an influence of the concentration of $O_2$ corresponding to each of the air-fuel ratios A/F. At the same concentration of $NO_x$, the air-fuel ratio A/F is increased, namely, if the concentration of $O_2$ is risen, the resistance value of the $NO_x$ sensor 5 is increased by an increment depending upon the concentration of $O_2$.

To cope with such a phenomenon, a concentration of $O_2$ corresponding to an air-fuel ratio A/F is measured, and a resistance value of the $NO_x$ sensor 5 corresponding to the concentration of $O_2$ is calculated and subtracted from the measured resistance value. This makes it possible to determine a high-accuracy sensitivity $R_{NO}$ to $NO_x$.

Figure 15:
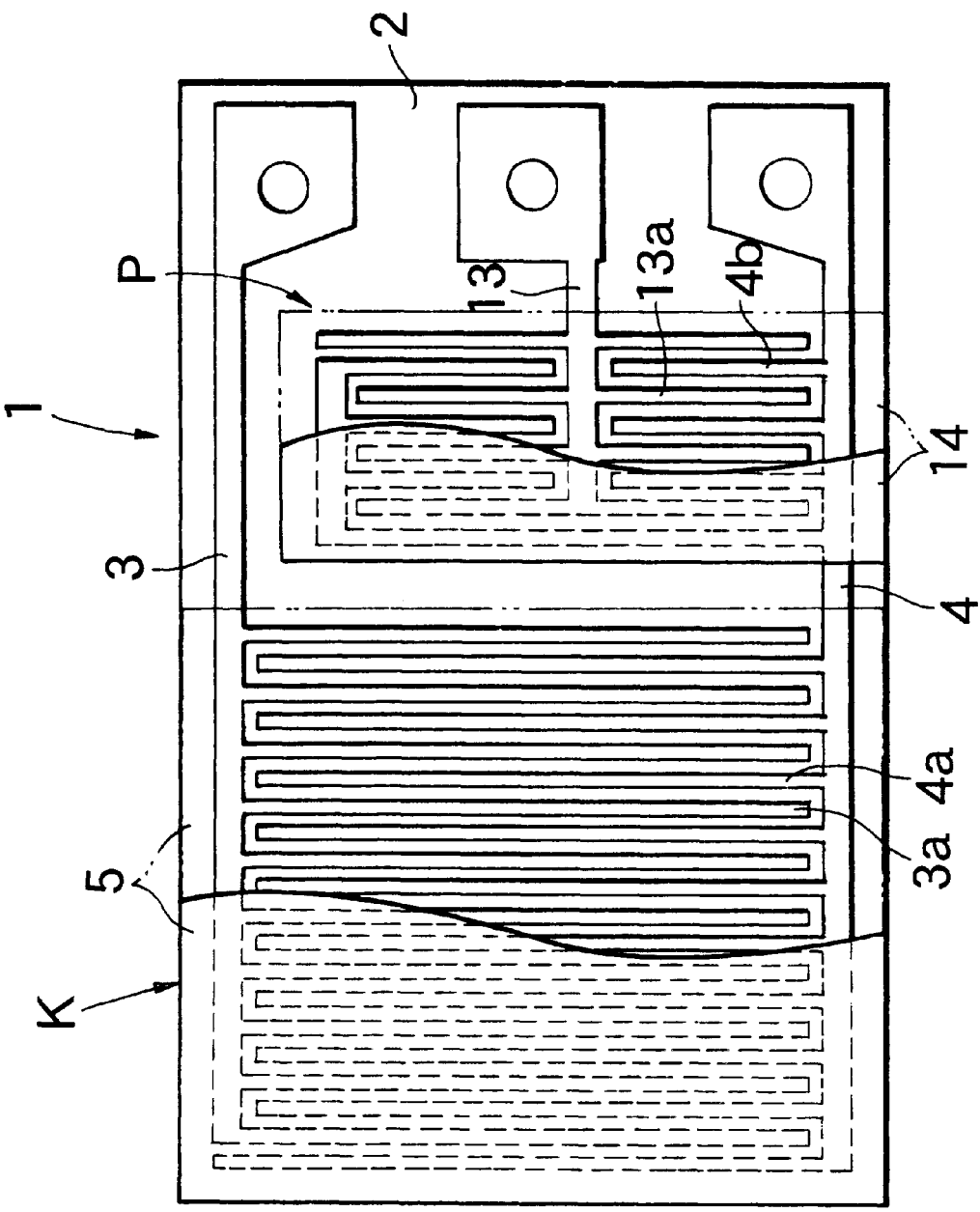
FIG. 15 is a plan view of a third example of an $NO_x$ measuring element.

FIG. 15 shows a modification to the $NO_x$ measuring element 1. This $NO_x$ measuring element 1 includes an $NO_x$ measuring element region K having a structure similar to that described above, and a correcting $O_2$ measuring element region P.

The correcting $O_2$ measuring element region P is comprised of a substrate 2 made of $Al_2O_3$ and common to the $NO_x$ measuring element region K, a pair of thin film-shaped electrodes 4 and 13 made of Pt, which have comb-shaped portions 4b and 13a disposed so that they are meshed with each other and which are adhered to a surface of the substrate 2, a thin film-shaped semiconductor-type $O_2$ sensor 14 adhered to the comb-shaped portions 4b and 13a and the substrate 2 to cover the comb-shaped portions 4b and 13a. One, namely electrode 4, of the electrodes is common to the $NO_x$ measuring element region K. A heater is provided on a back of the substrate 2.

With such $NO_x$ measuring element 1, the sensitivity to $NO_x$ can be corrected by the sensitivity to $O_2$ to determine a high-accuracy sensitivity to $NO_x$.

The $O_2$ sensor 14 is an oxide mixture which consists of 99.5 atom % of β-type $Nb_2O_5$ and 0.5 atom % of Cu.

The $O_2$ measuring element region P and thus the $O_2$ measuring element P (for convenience, the same reference character is used) was produced using the following process.

(a) Dehydrated ethanol was added to niobium ethoxide [Nb(OC$_2$H$_5$)$_5$] (made by Soekawa Chemicals Co. Ltd.) and then, copper ethoxide [Cu(OC$_2$H$_5$)$_2$] (made by Soekawa Chemicals Co. Ltd.)was added thereto to provide a liquid mixture.

(b) Pure water was added to the liquid mixture, while mixing the liquid mixture, and the resulting mixture was dried at 110° C. to provide a powder.

(c) The powder was subjected to a drying treatment at 100° C. for 2 hours and then to a calcination at 500° C. for 30 minutes to provide an oxide mixture consisting of α-type Nb$_2$O$_5$ and 0.5 atom % of Cu.

(d) 60 Grams of the oxide mixture was mixed with a solution of ethyl cellulose in α-terpineol to provide a printing paste.

(e) As shown in FIG. 15, using the printing paste, a screen printing was carried out on the substrate 2 having the pair of electrodes 4 and 13 to cover the comb-shaped portions 4b and 13a, thereby forming a thin film.

(f) The substrate 2 having the thin film was subjected to first, second, third and fourth heating treatments, in the same manner as described above, to provide an O$_2$ measuring element P including an O$_2$ sensor 14 made of β-type Nb$_2$O$_5$ and Cu. This is called an example 1.

Using, as a printing paste, a mixture of 60 grams of an α-type Nb$_2$O$_5$ powder resulting from the pulverization of α-type Nb$_2$O$_5$ having a purity of 99.9% (made by Soekawa Chemicals Co. Ltd.) for 3 hours in a planetary ball mill and 40 grams of a solution of ethyl cellulose in α-terpineol, a screen printing similar to that described above and a stepwise heating treatment were carried out to produce an O$_2$ measuring element formed of β-type Nb$_2$O$_5$. This is called an example 2.

Using the examples 1 and 2 of the O$_2$ measuring elements P, the following measurement of O$_2$ and NO$_x$ sensitivities were carried out.

First, the O$_2$ measuring element P heated to 450° C. by a heater was placed into an N$_2$ atmosphere having a temperature of 450° C. to measure a resistance R$_N$ using a multi-meter. Then, the O$_2$ measuring element P was placed into an atmosphere of a base gas comprised of 500 ppm of NO$_x$ and the balance of N$_2$ with varied concentrations of O$_2$ and maintained at 450° C. to measure a resistance value R$_{NO}$ using a multi-meter.

The sensitivities of the O$_2$ sensor 14 to O$_2$ and NO$_x$ were calculated according to the following equations:

$$O_2 \text{ sensitivity} = R_O/R_N, \text{ and } NO_x \text{ sensitivity} = R_{NO}/R_N$$

Figure 16:
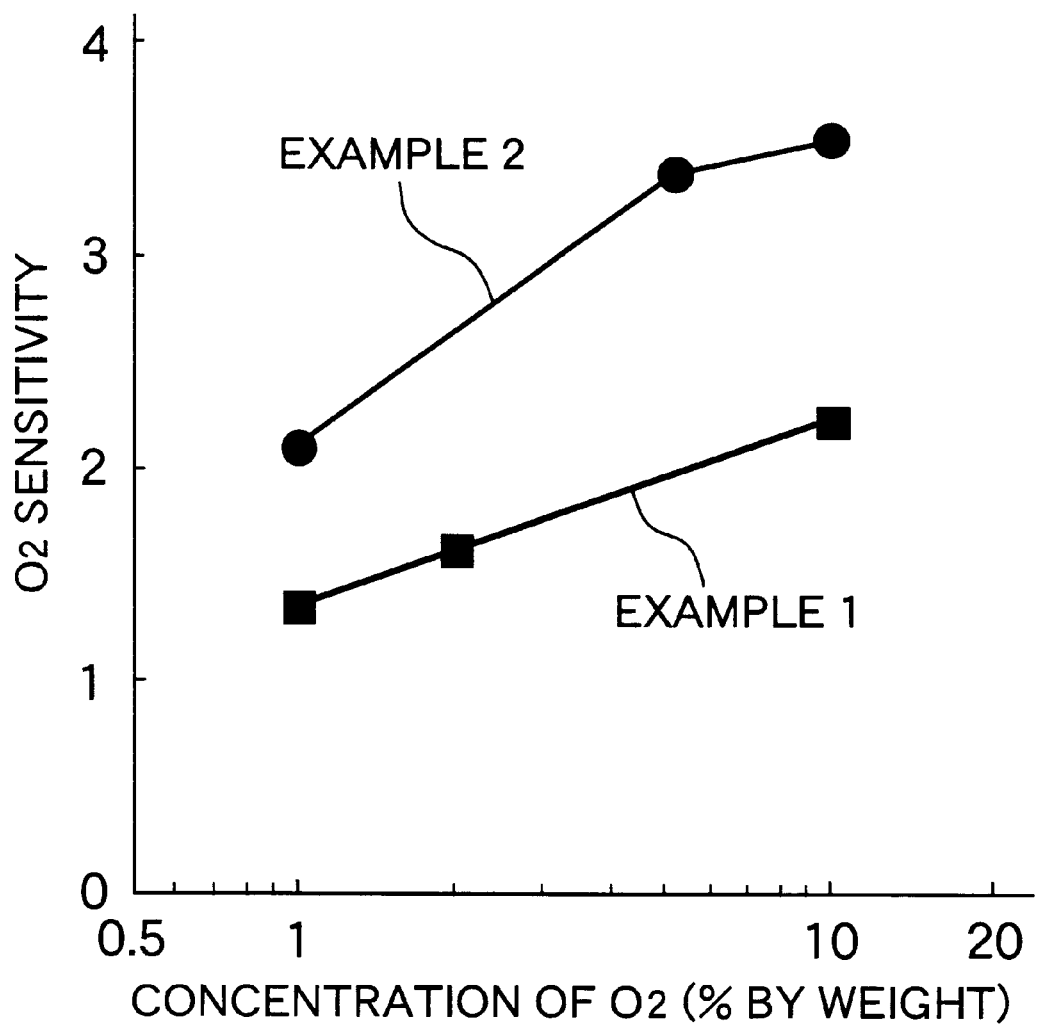
FIG. 16 is a graph illustrating the relationship between the concentration of $O_2$ and the sensitivity to $O_2$.
Figure 17:
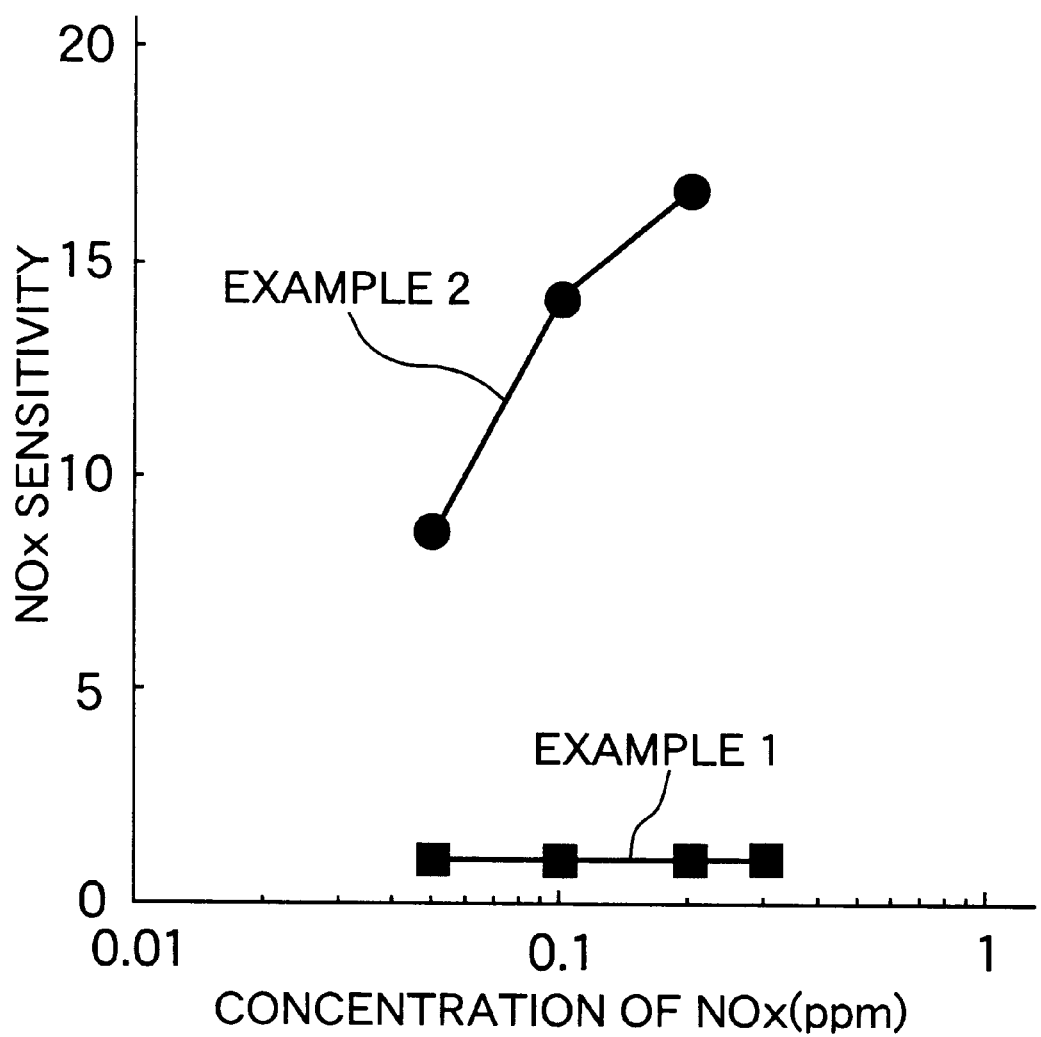
FIG. 17 is a graph illustrating the relationship between the concentration of $NO_x$ and the sensitivity to $NO_x$.

FIG. 16 shows the O$_2$ sensitivity, and FIG. 17 shows the NO$_x$ sensitivity. As is apparent from FIGS. 16 and 17, if the example 1 including the O$_2$ sensor P containing β-type Nb$_2$O$_5$ and 0.5 atom % of Cu was compared with the example 2 including the O$_2$ sensor P formed of only β-type Nb$_2$O$_5$, the example 1 is relatively high in sensitivity to O$_2$ and extremely low in sensitivity to NO$_x$. On the other hand, the example 2 is high in both of sensitivities to O$_2$ and NO$_x$. In this way, the example 1 is available as the O$_2$ measuring element, because of the low sensitivity to NO$_x$ which is an obstacle to the measurement of the concentration of O$_2$.

Various O$_2$ measuring elements P with varied contents of Cu in O$_2$ sensors 14 were produced in the same manner as that described above and were used for measurement of sensitivities to O$_2$ and NO$_x$ under conditions similar to those described above to provide the results shown in FIG. 18, in which the sensitivities to O$_2$ and NO$_x$ are shown by resistance valves R$_O$ and R$_{NO}$ respectively.

Figure 18:
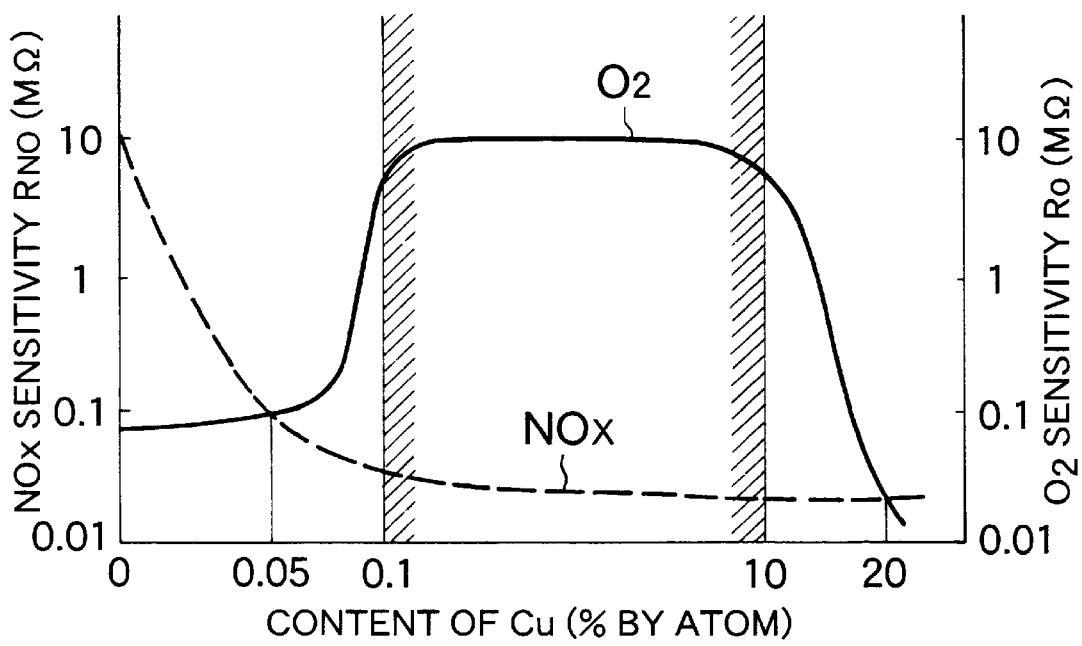
FIG. 18 is a graph illustrating the relationship between the content of Cu, the sensitivity $R_{NO}$ to $NO_x$ and the sensitivity $R_O$ to $O_2$.

As apparent from FIG. 18, if the content of Cu is set in a range of 0.1 atom %$\leq$Cu$\leq$10 atom %, the O$_2$ sensitivity R$_O$ can be increased, and the NO$_x$ sensitivity R$_{NO}$ can be reduced extremely.

If a particular amount of Cu is contained in β-type Nb$_2$O$_5$, it is believed that the sensitivity of the O$_2$ sensor 14 to NO$_x$ is reduced, for example, because the adsorbing characteristic of the O$_2$ sensor 14 is changed, and the decomposition of the NO$_x$ by a catalytic effect of Cu is produced.

What is claimed is:

1. An NO$_x$ sensor for an exhaust gas, which is made by sintering a plurality of columnar crystals of β-type Nb$_2$O$_5$, an average value M of aspect ratios b/a (wherein a represents a width, and b represents a length) in the columnar crystals being in a range of 2.11<M$\leq$5.

2. An NO$_x$ sensor for an exhaust gas according to claim 1, wherein further including TiO$_2$ in a content set in a range of 0.1% by weight$\leq$TiO$_2$$\leq$20% by weight.

3. A process for producing an NO$_x$ sensor for an exhaust gas, comprising the steps of subjecting a powder comprised of an aggregate of α-type Nb$_2$O$_5$ particles to a first heating treatment at a heating temperature T$_3$ set in a range of 600° C.$\leq$T$_3$$\leq$890° C., thereby producing the coalescence of the plurality of α-type Nb$_2$O$_5$ particles to produce a plurality of larger particles of α-type Nb$_2$O$_5$; and subjecting the powder resulting from said first heating treatment to a second heating treatment at a heating temperature T$_4$ set in a range of 950° C.$\leq$T$_4$$\leq$1,200° C., thereby producing the transformation of the α-type Nb$_2$O$_5$ into β-type Nb$_2$O$_5$ and the coalescence of the larger particles to grow a plurality of columnar crystals of β-type Nb$_2$O$_5$, and sintering the columnar crystals.

4. An NO$_x$ sensor for an exhaust gas, comprising, a substrates having a pair of electrodes for measuring resistance, a film formed of a plurality of columnar crystals of β-type Nb$_2$O$_5$ on said substrate and covering said electrodes, said columnar crystals having an average value M of aspect ratios b/a, wherein a represents a width and b represents a length, in a range of 2.11<M$\leq$5.

5. An NO$_x$ sensor of an exhaust gas according to claim 4, further including TiO$_2$ in said film in a content set in a range of 0.1% by weight$\leq$TiO$_2$$\leq$20% by weight.

6. The NO$_x$ sensor for an exhaust gas according to claim 4, wherein a thermistor is formed on said substrate for measuring the temperature of the substrate, and means for correcting a reading of the NO$_x$ sensor based on a variation of the temperature from a standard temperature.

7. The NO$_x$ sensor for an exhaust gas according to claim 6, wherein said standard temperature is 300° C.

8. The NO$_x$ sensor for an exhaust gas according to claim 4, wherein an oxygen sensor is formed on said substrate for measuring the oxygen concentration in the exhaust gas, and means for correcting a reading of the NO$_x$ sensor based on the oxygen concentration measured by said oxygen sensor.

9. The NO$_x$ sensor for an exhaust gas according to claim 8, wherein said oxygen sensor is comprised of a film of β-type Nb$_2$O$_5$ and Cu.

10. The NO$_x$ sensor for an exhaust gas according to claim 9, wherein the Cu is present in a content of from 0.1 atom % to 10 atom %.

11. The NO$_x$ sensor for an exhaust gas according to claim 4, wherein the NO$_x$ sensor is aged for at least 10 hours.

12. A process for producing an NO$_x$ sensor for an exhaust gas, comprising the steps of:

printing a paste of α-type Nb$_2$O$_5$ particles and a binder solution on a substrate having a pair of electrodes;

subjecting the paste and substrate to a primary heating treatment in a range of 100° C. to 200° C.;

subjecting the paste and substrate to a secondary heating treatment in a range of 370° C. to 470° C.;

subjecting a powder of an aggregate of α-type $Nb_2O_5$ particles remaining from the paste after the primary and secondary heating treatments to a third heating treatment at a heating temperature in a range of 600° C. to 890° C., thereby producing a coalescence of the plurality of α-type $Nb_2O_5$ particles to produce a plurality of larger particles of α-type $Nb_2O_5$; and subjecting the powder resulting from said third heating treatment to a fourth heating treatment at a heating temperature in a range of 950° C. to 1,200° C., thereby producing a transformation of the α-type $Nb_2O_5$ into β-type $Nb_2O_5$ and the coalescence of the larger particles to grow a plurality of columnar crystals of β-type $Nb_2O_5$, and sintering the columnar crystals.

13. A process for producing an $NO_x$ sensor for an exhaust gas, comprising the steps of sintering a plurality of columnar crystals of β-type $Nb_2O_5$ to have an average value M of aspect ratios b/a, wherein a represents a width and b represents a length, in the columnar crystals in a range of $2.11 < M \leq 5$.

14. A process for producing an $NO_x$ sensor for an exhaust gas according to claim 13, further including a step of adding, before sintering, $TiO_2$ in a content set in a range of 0.1% by weight $\leq TiO_2 \leq 20\%$ by weight.

15. A process for producing an $NO_x$ sensor for an exhaust gas according to claim 14, further subjecting the columnar crystals to a heating treatment at a heating temperature in a range of 950° C. to 1,200° C., thereby producing the transformation of an α-type $Nb_2O_5$ into the β-type $Nb_2O_5$ and the coalescence of the larger particles to grow a plurality of columnar crystals of β-type $Nb_2O_5$.

* * * * *